US 12,304,816 B2

(12) United States Patent
Barnett et al.

(10) Patent No.: US 12,304,816 B2
(45) Date of Patent: May 20, 2025

(54) LOW CO2 EMISSIONS METHANOL PROCESS AND PRODUCTION APPARATUS

(71) Applicant: BD Energy Systems, LLC, Houston, TX (US)

(72) Inventors: Daniel Joseph Barnett, Katy, TX (US); Gregory Bryan Cargle, Burlington, TX (US); Shashi Prakash Singh, Sugar Land, TX (US); Venancz Laszlo Patrovics, Sugar Land, TX (US)

(73) Assignee: BD Energy Systems, LLC, Houston, TX (US)

( * ) Notice: Subject to any disclaimer, the term of this patent is extended or adjusted under 35 U.S.C. 154(b) by 0 days.

(21) Appl. No.: 18/261,653

(22) PCT Filed: Jan. 14, 2022

(86) PCT No.: PCT/US2022/012445
§ 371 (c)(1),
(2) Date: Jul. 14, 2023

(87) PCT Pub. No.: WO2022/155425
PCT Pub. Date: Jul. 21, 2022

(65) Prior Publication Data
US 2024/0308847 A1 Sep. 19, 2024

Related U.S. Application Data

(60) Provisional application No. 63/137,554, filed on Jan. 14, 2021.

(51) Int. Cl.
*C01B 3/52* (2006.01)
*B01D 53/047* (2006.01)
(Continued)

(52) U.S. Cl.
CPC .............. *C01B 3/52* (2013.01); *B01D 53/047* (2013.01); *B01D 53/265* (2013.01); *C07C 31/04* (2013.01);
(Continued)

(58) Field of Classification Search
CPC .............. C01B 3/52; C01B 2203/0216; C01B 2203/0283; C01B 2203/0475;
(Continued)

(56) References Cited

U.S. PATENT DOCUMENTS 4,522,157 A 6/1985 O'Sullivan et al.
4,681,603 A 7/1987 Spangler et al.
(Continued)

FOREIGN PATENT DOCUMENTS

FR 2949772 3/2011
WO WO-03018958 3/2003
(Continued)

OTHER PUBLICATIONS

Ingham Alan: "Reducing the Carbon Intensity of Methanol for Use as a Transport Fuel", Johnson Matthey Technology Review, vol. 61, No. 4. Oct. 1, 2017 (Oct. 1, 2017), p. 297.
(Continued)

*Primary Examiner* — Wayne A Langel
*Assistant Examiner* — Syed T Iqbal
(74) *Attorney, Agent, or Firm* — Daniel N. Lundeen; Lundeen & Lundeen PLLC

(57) ABSTRACT

Processes and apparatus for low-CO2 emissions methanol production using a high efficiency (>90%) reformer fired with a low-carbon fuel (C:H<0.03) to produce syngas. CO2 is removed from the syngas, and the CO2-lean syngas is fed to a methanol synthesis loop. A purge stream from the methanol synthesis loop is processed to recover a hydrogen-rich stream and a tail gas stream. The hydrogen-rich stream
(Continued)

is supplied as fuel to fire the reformer, along with a portion (<10%) of the tail gas, to produce a CO2-lean flue gas (<3 vol %, dry basis). The flue gas is optionally cooled below a dew point to form condensate, which can be collected and removed. The methanol production can have a carbon efficiency of 97% or more, and a CO2 emissions reduction (compared to natural gas firing) of 88% or more.

26 Claims, 9 Drawing Sheets

(51) Int. Cl.
*B01D 53/26* (2006.01)
*C07C 31/04* (2006.01)
(52) U.S. Cl.
CPC .............................. *B01D 2257/504* (2013.01); *C01B 2203/0216* (2013.01); *C01B 2203/0283* (2013.01); *C01B 2203/0475* (2013.01)
(58) Field of Classification Search
CPC ............ C01B 2203/0288; C01B 3/384; C01B 2203/0233; C01B 2203/0415; C01B 2203/061; C01B 2203/0822; C01B 2203/0894; C01B 2203/1241; C01B 2203/127; C01B 3/56; B01D 53/047; B01D 53/265; B01D 2257/504; C07C 31/04; C07C 29/86; C07C 29/1518
See application file for complete search history.

(56) References Cited

U.S. PATENT DOCUMENTS

| | | |
|---|---|---|
| 4,705,101 A | 11/1987 | Warner |
| 4,732,740 A | 3/1988 | Woebcke et al. |
| 5,264,202 A | 11/1993 | Snyder |
| 5,787,821 A | 8/1998 | Bhat et al. |
| 5,826,518 A | 10/1998 | Bhat et al. |
| 6,159,395 A | 12/2000 | Early et al. |
| 6,191,174 B1 | 2/2001 | Early et al. |
| 8,496,908 B1 | 7/2013 | Genkin et al. |
| 2003/0092780 A1 | 5/2003 | Sogge et al. |
| 2004/0034110 A1 | 2/2004 | Grobys et al. |
| 2008/0141648 A1 | 6/2008 | Towler et al. |
| 2008/0308769 A1 | 12/2008 | Marty et al. |
| 2009/0117024 A1 | 5/2009 | Weedon et al. |
| 2009/0246118 A1 | 10/2009 | Drnevich et al. |
| 2010/0080754 A1 | 4/2010 | Fischer et al. |
| 2010/0158776 A1 | 6/2010 | Drnevich et al. |
| 2010/0310949 A1 | 12/2010 | Licht et al. |
| 2011/0100214 A1 | 5/2011 | Grover |
| 2011/0291425 A1 | 12/2011 | Juranitch |
| 2011/0313064 A1 | 12/2011 | Panza et al. |
| 2012/0039794 A1 | 2/2012 | Catchpole |
| 2012/0291481 A1 | 11/2012 | Terrien et al. |
| 2013/0097929 A1 | 4/2013 | Pham et al. |
| 2013/0156686 A1 | 6/2013 | Vauk et al. |
| 2020/0002166 A1 | 1/2020 | Warta et al. |
| 2022/0219975 A1 | 7/2022 | Feinstein |

FOREIGN PATENT DOCUMENTS

| | | | |
|---|---|---|---|
| WO | WO-2019238635 | 12/2019 | |
| WO | WO-2020148378 | 7/2020 | |
| WO | WO-2020148378 A1 * | 7/2020 | ............ C01B 3/382 |
| WO | WO2022040677 | 2/2022 | |
| WO | WO2022104375 | 5/2022 | |
| WO | WO2022155434 | 7/2022 | |

OTHER PUBLICATIONS

Pelligrini, Laura A.: "Design of the CO2 Removal Section for PSA Tail Gas Treatment in a Hydrogen Production Plant", Frontiers in Energy Research, Vo 8 Art 77 May 27, 2020.

\* cited by examiner

LOW CO2 EMISSIONS METHANOL PROCESS AND PRODUCTION APPARATUS

CROSS-REFERENCE TO RELATED APPLICATION

The instant application is a non-provisional of and claims the benefit of priority to U.S. Ser. No. 63/137,554, filed Jan. 14, 2021.

FIELD

The instant invention relates to processes and equipment to produce methanol with low CO2 emissions.

BACKGROUND

The production of methanol via synthesis gas generally involves the combustion or other oxidation of a hydrocarbon with the concomitant generation of CO2 which is sooner or later discharged to the atmosphere. In flue gas, CO2 is difficult to capture because of the low pressures involved, generally only slightly above atmospheric, and because of the acidic nature of flue gas condensate. Acidic condensate also imposes a requirement that condensation is generally avoided in the flue gas handling equipment, and, as a consequence, waste heat is not recovered below the dew point of the flue gas.

U.S. Pat. No. 6,159,395 discloses a compact reformer fired by combusting a hydrogen-rich fuel from an unidentified source with humidified air. The humidification of the combustion air, however, reduces the flame temperature to avoid metal dusting and thus reduces efficiency of the reforming.

U.S. Pat. No. 6,191,174 discloses a low-conversion reforming zone said to comprise a compact reformer operated at a low steam:carbon ratio, high pressure, and low temperature to produce synthesis gas for a once-through, low-conversion, low-pressure methanol synthesis reactor. The synthesis gas feed to the methanol synthesis zone comprises carbon dioxide and is stoichiometric, i.e., it contains two moles of hydrogen for each mole of carbon monoxide and three moles of hydrogen for each mole of carbon dioxide. Unreacted synthesis gas is separated using a membrane to recover a hydrogen-rich stream recycled to fuel; and a carbon oxide or methane-rich stream is recycled to the natural gas feed stream. A purge to fuel may be taken from the carbon oxide or methane-rich stream.

Other references of interest include US2013156686A1; US2012291481A1; FR2949772A1; US2010310949A1; US2010158776A1; US2010080754A1; US2009117024A1; US2020002166A1; US8496908B2; US2013097929A1; US2009246118A1; US2011100214A1; US5264202; US2012039794A1; US2011313064A1; US2004034110A1; US2003092780A1; Pelligrini, Laura A., "Design of the CO2 Removal Section for PSA Tail Gas Treatment in a Hydrogen Production Plant," Front. Energy Res., 27 May 2020, doi.org/10.3389/fenrg.2020.00077.

The industry is in need of ways to reduce or eliminate CO2 and other emissions, and/or ways to recover waste heat at temperatures below the dew point of the flue gas and/or that addresses one or more of the problems in the prior art.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Applicant has discovered ways to reduce CO2 emissions in a methanol production process and apparatus by removing CO2 from the syngas and processing a purge stream from the methanol synthesis loop to recover hydrogen as a source of a low-carbon fuel to fire the steam methane reformer (SMR). This design adds a CO2 capture step before the methanol reactor. Because CO2 can be used as a reactant in methanol production, a CO2 removal system in the process stream is a counter-intuitive addition to a methanol plant. The syngas, which is at a higher pressure than the flue gas, lends itself to more easily recovering CO2 (relative to low pressure flue gas) using an absorber-stripper unit with a solvent such as, for example, DMEA. A tail gas from the hydrogen recovery, comprising CO and/or CO2, can be supplied mostly with the hydrocarbon feed stock to the reformer, and a minor portion of the tail gas can be purged to the low-carbon fuel stream.

The duty of the reformer can be increased slightly relative to a natural gas fired reformer to produce the additional hydrogen required for the fuel.

For example, a base case reforming 1800 MMBtu/hr of natural gas and burning 74 MMBtu/hr natural gas for primary reforming now in a modified case according to embodiments herein reforms 1918 MMBtu/hr and uses 0 natural gas feed to the reformer combustion (except for CH4/CO present in a small amount of the tail gas). A typical SMR configuration would have led the skilled person in this field to conclude that the firing (i.e., energy requirement) in the radiant section would be too high to reform the additional amount of feed necessary to provide for the hydrogen firing, and thus it would be perceived as not cost effective. In the present design example, the inclusion of a higher-than-typical level of pre-reforming can meet the reforming requirement with only a small increase in heat release (~2.35% in this example). High hydrogen firing has a higher flame temperature, which is advantageous in improving radiant efficiency. In this manner, an improved efficiency of the reformer is obtained due to the higher flame temperature from using hydrogen. The radiant outlet temperature (1650° F. in this example) can be substantially higher than most methanol plant SMRs and even higher than some hydrogen plant SMRs.

Moreover, less flue gas, which now consists essentially of nitrogen and water vapor, leads to less waste heat leaving the stack, and essentially no sulfur in the fuel, due to desulfurization of the feed, leads to a lower acid dew point which in turn leads to improved waste heat recovery from the flue gas. Moreover, less acid in the flue gas can facilitate the use of an optional condensing portion of the convection section where condensate can be collected and removed. In this manner, very low-level heat can be recovered from the flue gas, e.g., below 70° C. (158° F.) or below: 60° C. (140° F.), by employing an ambient temperature or cooled mixture of hydrocarbon and water. In heat exchange between the flue gas and the process stream, saturation of a hydrocarbon vapor with water, for example, facilitates cooling of the flue gas while the heat removed provides the latent heat to vaporize the water in the process stream, e.g., without increasing the temperature of the process stream. The saturated process stream can then be optionally further heated, e.g., superheated, and fed to a reactor in a radiant section of the fired heater.

In one aspect, the invention is embodied in a low-CO2 emission methanol process, comprising the steps of: (a) mixing a hydrocarbon feed stock with water to form a mixed feed stream: (b) reforming the mixed feed stream in a reforming furnace comprising a radiant section and a convection section to form a syngas stream: (c) supplying air (or oxygen-enriched air) and a carbon-lean fuel stream comprising hydrogen to fire the radiant section: (d) passing flue gas from the radiant section to the convection section: (e) cooling the flue gas in the convection section and optionally removing particulates from the flue gas: (f) discharging the cooled flue gas, wherein the flue gas is lean in CO2 (preferably less than 3 vol %, more preferably less than 1.5 vol %, and even more preferably less than 1 vol %, dry basis); (g) cooling the syngas stream; (h) passing the cooled syngas directly to (preferably no shift conversion) an absorber-stripper unit to produce a CO2 rich stream and a CO2-lean syngas stream; (i) compressing and passing the CO2-lean syngas stream to a methanol reactor loop to produce a methanol-rich stream, wherein the methanol reactor loop comprises a methanol synthesis reactor, a methanol recovery section to recover a crude methanol stream and a recycle syngas stream, and a recycle compressor to compress the recycle syngas stream to a pressure of the reactor, which is higher than a pressure of the mixed feed stream in step (b); (j) processing the crude methanol stream in a methanol wash unit to recover a methanol product, a condensate stream, and a fusel oil stream; (k) supplying a purge stream from the methanol reactor loop to a pressure swing adsorption unit to obtain a hydrogen-rich stream and a hydrogen-lean tail gas stream: (l) supplying the hydrogen-rich stream to the carbon-lean fuel stream in step (c); (m) supplying at least a portion (preferably 90% or more) of the tail gas stream from step (k) to the hydrocarbon feed stock in step (a); (n) purging a remaining portion (preferably no more than 10%) of the tail gas stream from step (m) to the carbon-lean fuel stream in step (c).

In another aspect, the invention is embodied in a low-CO2 emissions methanol production apparatus, comprising: a mixing station to mix a hydrocarbon feed stock with water and form a mixed feed stream: a reformer in a reforming furnace comprising a radiant section and a convection section to reform the mixed feed stream and form a syngas stream; an air line and a carbon-lean fuel stream to fire one or more burners in the radiant section; a flue to pass flue gas from the radiant section and through the convection section; one or more convection section heat exchangers to cool the flue gas in the convection section; a stack to discharge the cooled flue gas from the convection section, wherein the cooled flue gas is lean in CO2 (preferably less than 3 vol %, more preferably less than 1.5 vol %, and even more preferably less than 1 vol %, dry basis); one or more process heat exchangers to cool the syngas stream; an absorber-stripper unit to receive the cooled syngas stream and produce a CO2 rich stream and a CO2-lean syngas stream; a compressor to recirculate the CO2-lean syngas stream in a methanol reactor loop and produce a methanol-rich stream; a pressure swing adsorption unit to receive a purge stream from the methanol reactor loop to produce a hydrogen-rich stream and a hydrogen-lean tail gas stream; a line to supply the hydrogen-rich stream from the pressure swing adsorption unit to the one or more burners; a line to supply at least a portion (preferably at least 90%) of the tail gas stream to the hydrocarbon feed stock; and a line for purging a remaining portion (preferably no more than 10%) of the tail gas stream to the carbon-lean fuel stream.

DETAILED DESCRIPTION

Figure 1:
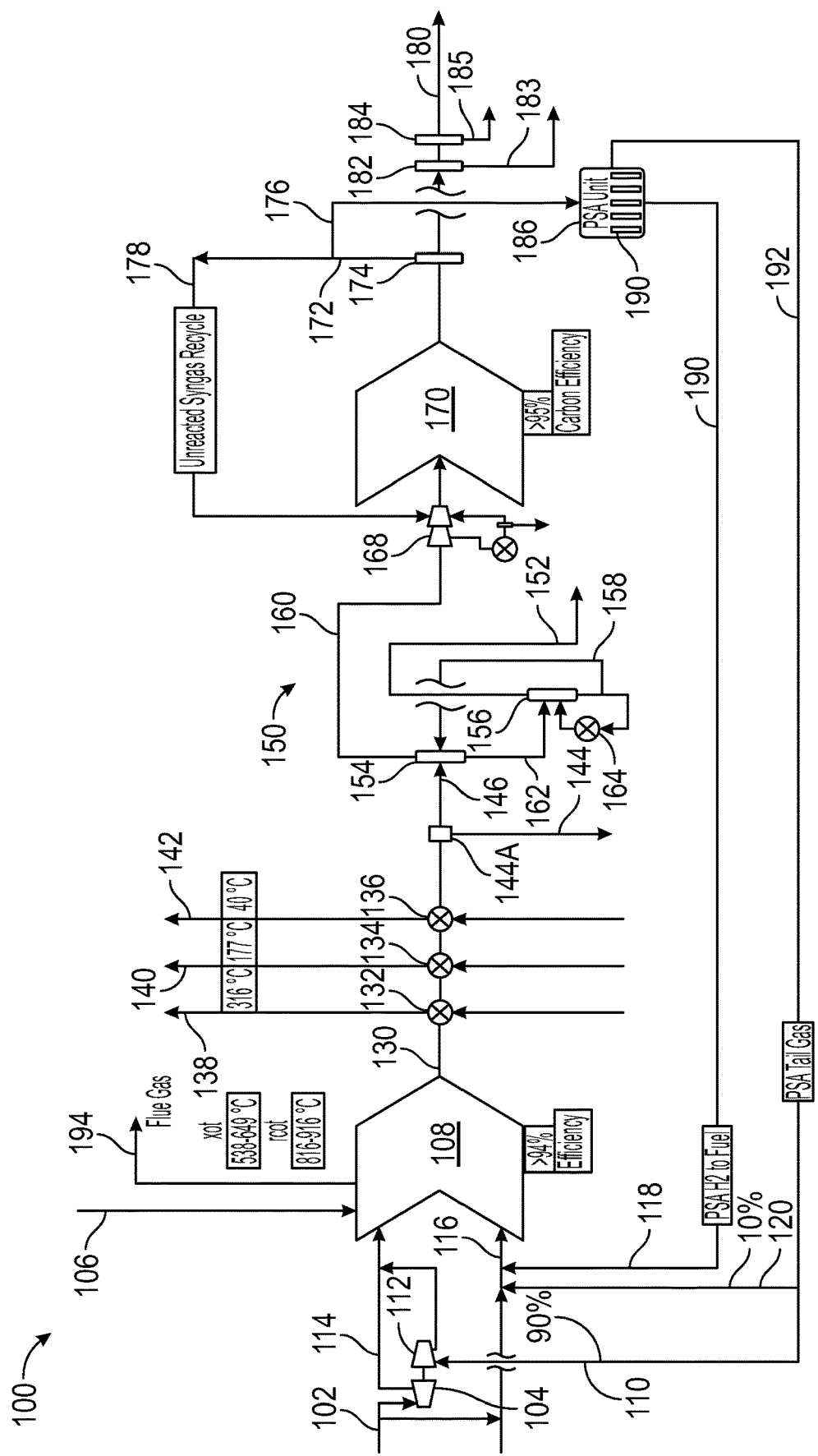
FIG. 1 is a block diagram illustrating a low-CO2 emissions methanol process and production equipment according to embodiments disclosed herein.

Descriptions and examples presented herein are solely for the purpose of illustrating preferred embodiments and should not be construed as limiting a scope of applications of this invention. While the methods and apparatus are described herein as using certain process approaches or design elements, their actual realization could optionally comprise two or more different process approaches or design elements. In addition, the process approaches and design elements can also comprise some components other than the ones cited.

Throughout the entire specification, including the claims, the following terms shall have the indicated meanings. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of the present invention described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B): in another embodiment, to B only (optionally including elements other than A): in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of".

Comprising: In the claims, as well as in the specification, all transitional phrases such as "comprising." "including." "carrying." "having." "containing." "involving." "holding." "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any process or apparatus described herein can be comprised of, can consist of, or can consist essentially of any one or more of the described elements. Moreover, steps in a process may be carried out in any order and are not limited to the order in which they are listed.

For purposes herein, the carbon efficiency of a methanol loop is defined as the ratio of carbon in the methanol in the product stream divided by the total sum of carbon in all of the product streams, including any purge stream.

For purposes herein, "cold air" refers to air at or near (+20° C.) ambient temperature or colder and "low-humidity" air refers to air having a relative humidity at ambient temperature less than 80%, preferably less than 60%.

A "condensing convection section" refers to a portion of the flue gas treatment system in which heat exchange results in at least partial condensation of the flue gas, i.e., the temperature is reduced to the dew point of the flue gas or below. A "non-condensing convection section" refers to a portion of the flue gas treatment system in which heat exchange does not result in condensation, i.e., the flue gas is maintained above its dew point.

For purposes herein, a "convection section" refers to the cooler portion of a furnace wherein heat transfer is predominantly by convection, as opposed to radiation.

For purposes herein, the crossover temperature (XOT) refers to the temperature of the mixed feed stream (natural gas and steam) crossing from the convection preheat to the reformer catalyst tube, and the outlet temperature (RCOT) refers to the outlet temperature from the radiant catalyst tubes.

For purposes herein, a "desulfurizer vessel" refers to a reactor, drum, column, or other enclosure in a sulfur removal system utilized to remove sulfur compounds from a process stream. Desulfurization is a well-known treatment process that removes sulfur by scrubbing with an alkali solid such as, for example, nickel molybdate and zinc oxide, or alkali solution, e.g., wet scrubbers using venturi-rod scrubbers, packed bed scrubbers, and/or spray towers, scrubbing with sodium sulfite solution, gas phase oxidation and ammonia reaction, or the like.

As used herein, "directly" refers to a process step that occurs without any substantial intervening step.

For purposes herein, "downstream" refers to a location in a fluid flow path spaced away from the reference location in the direction of flow, and "upstream" in the direction against flow: Unless otherwise stated herein, the terms "upstream" and "downstream" as applied to equipment or locations in the convection section are used in reference to the direction of the flue gas flow.

For purposes herein, the efficiency of a reformer is defined as the total reformer duty divided by the total reformer firing.

As used herein, "fired heater" refers to a furnace unit in which a fluid stream is heated by one or more fuel burners in a firebox, and includes where present, the flue gas treatment system up to discharge to the atmosphere. The mixture of effluent gases resulting from the combustion is referred to herein as the "flue gas." The heating may be effected by passing the fluid through tubes disposed in the firebox, which is dominated by radiant heat transfer and referred to herein as the "radiant section." Additional heat may be recovered from a section dominated by convection, i.e., the "convection section." Steam-methane reformers are used in the following discussion as one non-limiting example of a fired heater.

For purposes herein, a "fusel oil" is a mixture of alcohols heavier than methanol.

For purposes herein, the term "heat exchanger" refers to an indirect heat transfer unit in which one stream is put into thermal communication with another stream while maintaining physical separation between the streams. An "interchanger" refers to a heat exchanger in which a feed stream to a unit or stage is heated or cooled against an effluent stream from that unit or stage.

A "heat exchanger coil" refers to a tubular structure used in a heat exchanger to separate one stream passing through the tubular structure from another stream passing across an exterior surface of the tubular structure. The fluid flowing through the coil is referred to as the "coil fluid." A coil or heat exchanger may comprise one or more rows of one or more tubes or other conduits forming one or more pathways there-through to allow heat transfer between fluid flowing through the conduit and another fluid in thermal communication with the heat exchanger.

For purposes herein, "heat exchange relationship" means that a first material, stream, or unit receives heat directly or indirectly from a second material, stream, or unit.

For purposes herein, a "methanol reactor loop" refers to the system of reacting syngas in a reactor to produce methanol, separating a methanol rich stream from the reactor effluent, and recirculating unreacted materials to the reactor.

For purposes herein, "pressure swing adsorption" or PSA refers to a technology used to separate some gas species from a mixture of gases under pressure according to the species' molecular characteristics and affinity for an adsorbent material. It typically but not necessarily operates at near-ambient temperatures. Specific adsorbent materials (e.g., zeolites, activated carbon, molecular sieves, etc.) are used as a trap, preferentially adsorbing the target gas species at high pressure. The process then swings to low pressure to desorb the adsorbed material.

For purposes herein, processing, reacting, and/or treatment of material or process stream refers to any process that chemically or physically alters properties of a starting material. As used herein, a "process stream" refers to a stream or line comprising reactants, intermediates, and/or products used in a process. The terms "stream" and "line" are used interchangeably herein. As used herein, "hydrocarbon" refers to any compound comprising carbon and hydrogen. As used herein, unless otherwise indicated or the context requires, "water" refers collectively to ice, liquid water, aqueous solutions and mixtures, water vapor, and/or steam. "Fluid" refers to gases, liquids, supercritical fluids, combinations thereof such as emulsions, foams, mists, and the like, and may also contain entrained solids.

For purposes herein, a "purge" refers to a stream withdrawn from a recirculatory system that prevents inerts from building up in the system.

For purposes herein, a "radiant section" refers to the hotter portion of a furnace wherein heat transfer is predominantly by radiation, as opposed to convection.

For purposes herein, a "reformer" refers to an apparatus, including a primary reformer and any pre-reformers and/or secondary reformers, in which a hydrocarbonaceous feedstock and steam are reformed to produce a synthesis gas. A "primary reformer" refers to a reformer which is heated primarily by oxidation, e.g., internally or directly heated by partial oxidation as in an autothermal reformer or in a partial oxidation reformer, or indirectly by external combustion, e.g., fired externally of the process gas (i.e., the process gas is not exposed directly to the flame). A "secondary reformer" refers to a "post-reformer" in which the primary reformer effluent is subjected to further reforming. A "pre-reformer" refers to a reformer in which the feedstock is partially reformed prior to primary reforming.

For purposes herein, "selective catalytic reduction" or SCR refers to a means of converting nitrogen oxides, also referred to as NOx, with the aid of a catalyst into diatomic nitrogen (N2), and water (H2O). A reductant, typically anhydrous ammonia, aqueous ammonia or urea solution, is typically added to a stream of flue or exhaust gas and is absorbed onto the catalyst.

For purposes herein, "shift conversion" means the step of passing a syngas mixture through a shift converter to react water and CO to produce CO2 and hydrogen. A "shift converter" is a physical reactor designed or intended to primarily promote the water-gas shift conversion reaction. The shift conversion can occur at high temperature, low temperature, or intermediate temperature.

A "superalloy," also known as a high-performance alloy, is a metallurgical alloy that exhibits several key characteristics: excellent mechanical strength, resistance to thermal creep deformation, good surface stability and resistance to corrosion or oxidation. The crystal structure is typically but not necessarily face-centered cubic austenitic. For purposes herein, a scrubbing agent refers to a material or combination of materials which have or impart removal of components upon contact of the material with a vapor stream, e.g., absorbents, reactants, and so on. Typical examples for aqueous scrubbing of flue gas components, e.g., $CO_2$, CO, NOx, $NO_2$, SOx, and the like, include ammonia, alkyl amines and alkanol amines having from 3 to 40 carbon atoms, sulfite, caustic soda, lithium hydroxide, calcium oxide (lime), urea, hydrogen peroxide, nitric acid, combinations thereof and the like.

For purposes herein, "synthesis gas" or "syngas" refers to a mixture of primarily hydrogen and carbon monoxide, e.g., from a reformer, but which may also comprise water and carbon dioxide.

In one aspect, the invention is embodied in a low-CO2 emission methanol process. The process comprises the steps of: (a) mixing a hydrocarbon feed stock with water to form a mixed feed stream: (b) reforming the mixed feed stream in a reforming furnace comprising a radiant section and a convection section to form a syngas stream: (c) supplying air and a carbon-lean fuel stream comprising hydrogen to fire the radiant section: (d) passing flue gas from the radiant section to the convection section: (e) cooling the flue gas in the convection section and optionally removing particulates from the flue gas; and (f) discharging the cooled flue gas. The flue gas is lean in CO2, preferably less than 3 vol %, more preferably less than 1.5 vol %, and even more preferably less than 1 vol % CO2, dry basis.

The process further comprises the steps of: (g) cooling the syngas stream; (h) passing the cooled syngas stream directly (preferably no shift conversion) through an absorber-stripper unit to produce a CO2 rich stream and a CO2-lean syngas stream; (i) compressing and passing the CO2-lean syngas stream to a methanol reactor loop to produce a methanol-rich stream, wherein the methanol reactor loop comprises a methanol synthesis reactor, a methanol recovery section to recover a crude methanol stream and a recycle syngas stream, and a recycle compressor to compress the recycle syngas stream to a pressure of the reactor, which is higher than a pressure of the mixed feed stream in step (b); (j) processing the crude methanol stream in a methanol wash unit to recover a methanol product; (k) supplying a purge stream from the methanol reactor loop to a pressure swing adsorption unit to obtain a hydrogen-rich stream and a hydrogen-lean tail gas stream: (l) supplying the hydrogen-rich stream to the carbon-lean fuel stream in step (c); (m) supplying at least a portion of the tail gas stream from step (k) to the hydrocarbon feed stock in step (a); and (n) purging a remaining portion of the tail gas stream from step (l) to the carbon-lean fuel stream in step (c). Preferably, 90% or more of the tail gas stream is supplied to the hydrocarbon feed stock in step (a), and no more than 10% is supplied to the carbon-lean fuel stream in step (c).

In the foregoing embodiment or any other embodiment, the hydrocarbon feed stock can comprise a hydrogen-rich hydrocarbon such as naphtha or natural gas, preferably natural gas, and the mixed feed stream preferably comprises a molar ratio of steam to carbon from 1 to 5, more preferably from 1.8 to 2.5.

In the foregoing embodiment or any other embodiment, the reforming step (b) can comprise: (b-1) pre-reforming the mixed feed stream to form a partially reformed feed stream; and (b-2) primary reforming of the partially reformed feed stream in the radiant section of the reformer. In this or any other embodiment, the reforming step (b) can comprise: (B-1) supplying the mixed feed stream to a first pre-reformer to form a first partially reformed feed stream: (B-2) supplying the first partially reformed feed stream to a second pre-reformer to form a second partially reformed feed stream; and (B-3) passing the second partially reformed feed stream to the radiant section of the reforming furnace to produce the syngas stream. The pre-reforming can be in one or more pre-reformers in heat exchange relationship with the flue gas from the radiant section. The one or more pre-reformers can be disposed externally of the convection section, e.g., with respective feed pre-heat coils disposed in the convection section in heat exchange relationship with the flue gas from the radiant section.

In the foregoing embodiment or any other embodiment, the reforming step preferably has an efficiency of at least 90%, more preferably at least 92%, and even more preferably at least 94%. The reforming step (b) preferably comprises a crossover temperature of 566° C. (1050° F.) or less and a reformer outlet temperature of at least 902° C. (1655° F.). In this or any other embodiment, a ratio of air to fuel in step (c) preferably produces a flame temperature equal to or greater than 2500° K. The air is preferably not humidified, i.e., the air has low humidity so as to not substantially reduce the flame temperature.

In the foregoing embodiment or any other embodiment, the process can further comprise the steps of: (e-1) pre-heating the hydrocarbon feed stock in a first heat exchanger coil in the convection section: (e-2) wherein the mixing in step (a) comprises saturating the pre-heated hydrocarbon feed stock from step (e-1): (e-3) heating the mixed feed stream from step (e-2) with the flue gas in a second heat exchanger coil in the convection section upstream of the first heat exchanger coil with respect to flue gas flow through the convection section, to superheat the mixed feed stream: (e-4) pre-reforming the superheated mixed feed stream in one or more pre-reformers disposed in heat exchange relationship with the flue gas in the convection section upstream of the second heat exchanger coil with respect to flue gas flow to form a partially reformed stream, or in one or more pre-reformers disposed externally of the convection section and receiving pre-heated mixed feed from a pre-heat coil disposed in heat exchange relationship with the flue gas in the convection section upstream of the second heat exchanger coil with respect to flue gas flow to form the partially reformed stream: (e-5) optionally pre-heating the pre-reformed stream, in a third heat exchanger coil in the convection section upstream of the one or more pre-reformers with respect to flue gas flow through the convection section; and (b-2) reforming the partially reformed feed stream in the radiant section.

If desired, the process can further comprise the steps of: (e-6) selective catalytic reduction of the flue gas to remove nitrogen oxides; and (e-7) pre-heating cold air (e.g., ambient temperature) in a third heat exchanger coil in the convection section. The entire convection section can be maintained at a temperature above a dew point to inhibit condensate formation, or alternatively, the process can further comprise the steps of: (e-8) cooling the flue gas to below a dew point to form condensate in a condensing portion of the convection section; and (e-9) collecting and removing the condensate from the convection section.

In the foregoing embodiment or any other embodiment, the process can further comprise the steps of: (E-1) pre-heating the mixed feed stream in a first heat exchanger coil in a condensing portion of the convection section to cool the flue gas to below a dew point and form condensate: (E-2) collecting and removing the condensate from the convection section; (E-3) heating the pre-heated hydrocarbon feedstock from the first heat exchanger coil with the flue gas in a second heat exchanger coil in a non-condensing portion of the convection section upstream of the first heat exchanger coil with respect to flue gas flow through the convection section, to superheat the mixed feed stream; and (E-4) reforming the superheated mixed feed stream in at least the radiant section and optionally in a reforming exchanger in the convection section upstream of the second heat exchanger coil with respect to flue gas flow.

In the foregoing embodiment or any other embodiment, the process can further comprise: (E-5) recycling a portion of the collected condensate to the convection section to contact and scrub the flue gas downstream of the first heat exchanger coil; and or (E-6) collecting the recycled condensate with the condensate from the first heat exchanger coil; and or (E-7) cooling the recycled condensate prior to contact with the flue gas; and or (E-8) adding a scrubbing agent to the recycled condensate prior to contact with the flue gas; and or (E-9) regenerating at least a portion of the collected condensate to recover a carbon dioxide-rich stream and carbon dioxide-lean condensate for the recycling to the convection section; and or (E-10) passing the scrubbed flue gas through a demister to remove entrained liquid.

In the foregoing embodiment or any other embodiment, the process can further comprise: (E-11) preheating the hydrocarbon in a third heat exchanger coil located downstream of the first heat exchanger in the condensing portion of the convection section: (E-12) further preheating the hydrocarbon from the third heat exchanger coil in a fourth heat exchanger coil upstream of the second heat exchanger coil in the non-condensing portion of the convection section: (E-13) exchanging heat between the preheated hydrocarbon from the fourth heat exchanger coil and the preheated hydrocarbon from the third heat exchanger coil: (E-14) combining the hydrocarbon from the fourth heat exchanger coil with the water to form the mixed feed stream for heating in the first heat exchanger coil; and (E-15) desulfurizing the preheated hydrocarbon from the fourth heat exchanger coil prior to the mixing with the water in step (a). If desired, one of the first and second heat exchangers can be located in an essentially vertical convection flue section, and the other one of the first and second heat exchangers can be located in an essentially horizontal convection flue section.

In the foregoing embodiment or any other embodiment, the process can further comprise: (E-16) inducing a draft of the flue gas downstream of the second heat exchanger coil and upstream of the condensate collection and first heat exchanger coil, and discharging the flue gas downstream from the first heat exchanger into a stack; and or (E-17) diverting at least a portion of the flue gas, from a location that is downstream of the draft induction and upstream of the condensate collection and first heat exchanger coil, into the stack, and bypassing the condensate collection and first heat exchanger coil; and or (E-18) controlling the portion of the diverted flue gas using one or more flow dampers to regulate the flow of the diverted portion; and or (E-19) passing the flue gas downstream of the draft induction through a first portion of the stack, across the first heat exchanger coil, and then into a second portion of the stack located above the first portion, wherein at least one of the one or more dampers is located in the stack between the first and second portions of the stack.

In the foregoing embodiment or any other embodiment, the process can further comprise preheating air in an air preheat coil in the convection section and supplying the preheated air to a combustion burner in the radiant section in step (c).

In the foregoing embodiment or any other embodiment, step (g) can comprise generating steam, preheating boiler feed water, heat exchange with air or cooling water, or a combination thereof.

Preferably, the CO2-lean syngas stream in step (h) comprises less than 0.1 vol % CO2 or is preferably essentially free of CO2. Step (h) preferably comprises contacting the cooled syngas with a CO2 solvent, preferably an alkanolamine, more preferably methyl diethanolamine. For example, step (h) can comprise contacting the cooled syngas with the CO2 solvent in an absorber, wherein the CO2 is stripped from the solvent in a stripper, and wherein the stripper is operated at a lower pressure and/or a higher temperature than the stripper.

In the foregoing embodiment or any other embodiment, step (i) preferably comprises methanol synthesis with a carbon efficiency of equal to or greater than 95%, more preferably equal to or greater than 97%.

In the foregoing embodiment or any other embodiment, the carbon-lean fuel stream in step (c) preferably consists of or consists essentially of the hydrogen-rich stream from step (l) and the remaining portion of the tail gas stream from step (n). If desired, the hydrocarbon feed stock from step (a) and the portion of the tail gas stream from step (m) are supplied to the reforming step (b) at a rate wherein the reforming step (b) produces excess hydrogen for step (l) in an amount, together with the tail gas purge in step (n), that matches the fuel requirements in step (c).

In the foregoing embodiment or any other embodiment, the process can further comprise condensate stripping from the cooled syngas stream from step (g) upstream from the absorber-stripper unit in step (h), preferably wherein a fusel oil stream from step (j) is supplied to the condensate stripping step.

In another aspect, the invention is embodied in low-CO2 emissions methanol production apparatus. The apparatus comprises: a mixing station to mix a hydrocarbon feed stock with water and form a mixed feed stream: a reformer in a reforming furnace comprising a radiant section and a convection section to reform the mixed feed stream and form a syngas stream: an air intake and a carbon-lean fuel stream to fire one or more burners in the radiant section: a flue to pass flue gas from the radiant section and through the convection section; one or more convection section heat exchangers to cool the flue gas in the convection section: an optional particulate removal unit in the convection section to remove particulates from the flue gas: a stack to discharge the cooled flue gas from the convection section, wherein the cooled flue gas is lean in CO2 (preferably less than 3 vol %, more preferably less than 1.5 vol %, and even more preferably less than 1 vol %, dry basis); one or more process heat exchangers to cool the syngas stream: an absorber-stripper unit to directly receive (preferably without any shift converter) the cooled syngas stream and produce a CO2 rich stream and a CO2-lean syngas stream: a compressor to recirculate the CO2-lean syngas stream in a methanol reactor loop at a higher pressure than the reformer and produce a methanol-rich stream; a methanol wash unit to recover a methanol product, a condensate stream, and a fusel oil stream from the methanol-rich stream: a pressure swing adsorption unit to receive a purge stream from the methanol reactor loop to produce a hydrogen-rich stream and a hydrogen-lean tail gas stream: a line to supply the hydrogen-rich stream from the pressure swing adsorption unit to the one or more burners: a line to supply at least a portion (preferably 90%) of the tail gas stream to the hydrocarbon feed stock; and a line for purging a remaining portion (preferably 10%) of the tail gas stream to the carbon-lean fuel stream.

In various embodiments of the apparatus, the hydrocarbon feed stock can comprise a hydrogen-rich hydrocarbon such as naphtha or natural gas, preferably natural gas, and the mixed feed stream preferably comprises a molar ratio of steam to carbon from 1 to 5, more preferably from 1.8 to 2.5.

In the foregoing embodiment or any other embodiment of the apparatus, the reformer can comprise: one or more pre-reformers in convection heat exchange relationship with the flue gas from the radiant section receiving the mixed feed stream to form a partially reformed feedstock, or one or more pre-reformers disposed externally of the convection section and further comprising a preheat exchange coil disposed in the convection section to pre-heat the partially reformed stream from the one or more pre-reformers for supply to the primary reformer; and a primary reformer disposed in the radiant section to receive the partially reformed feedstock to produce the syngas stream. The one or more pre-reformers are preferably disposed externally of the convection section, and a preheat exchange coil can be disposed in the convection section to pre-heat the partially reformed stream from the one or more pre-reformers for supply to the primary reformer. Preferably, the reformer is operable with an efficiency of at least 90%, more preferably at least 92%, and even more preferably at least 94%. Preferably, the reformer is operable with a crossover temperature of 566° C. (1050° F.) or less and a reformer outlet temperature of at least 902° C. (1655° F.). Preferably, a ratio of air to fuel produces a flame temperature equal to or greater than 2500° K.

In the foregoing embodiment or any other embodiment, the apparatus can further comprise: a first heat exchanger coil in the convection section for pre-heating the hydrocarbon feed stock: a saturator for saturating the pre-heated hydrocarbon feed stock: a second heat exchanger coil in the convection section upstream of the first heat exchanger coil with respect to flue gas flow through the convection section, to superheat the mixed feed stream; one or more internal or external pre-reformers for pre-reforming the superheated mixed feed stream; an optional third heat exchanger disposed in the convection section upstream from the one or more pre-reformers with respect to flue gas flow to pre-heat the pre-reformed feed stream; and a line to supply the pre-reformed feed stream to the reformer. The apparatus preferably comprises a selective catalytic reduction unit downstream from the first heat exchanger coil with respect to flue gas flow through the convection section to remove nitrogen oxides from the flue gas; and a cold air preheater disposed downstream from the selective catalytic reduction unit with respect to flue gas flow through the convection section.

In the foregoing embodiment or any other embodiment, the entire convection section is free of condensate, or alternatively the apparatus can further comprise: a heat exchanger in the convection section for cooling the flue gas to below a dew point to form condensate in a condensing portion of the convection section; and a line for removing the condensate from the convection section.

In the foregoing embodiment or any other embodiment, the apparatus can further comprise: a first heat exchanger coil in a condensing portion of the convection section to pre-heat the mixed feed stream and cool the flue gas to below a dew point and form condensate: a reservoir to collect and a line to remove the condensate from the convection section: a second heat exchanger coil disposed in a non-condensing portion of the convection section upstream of the first heat exchanger coil with respect to flue gas flow through the convection section, to heat the preheated hydrocarbon feedstock from the first heat exchanger coil with the flue gas and superheat the mixed feed stream; and wherein the reformer comprises a pre-reformer and a primary reformer in the radiant section.

Preferably, the apparatus further comprises: a line for recycling a portion of the collected condensate to the convection section to contact and scrub the flue gas downstream of the first heat exchanger coil; and or a reservoir for collecting the recycled condensate with the condensate from the first heat exchanger coil; and or a heat exchanger for cooling the recycled condensate prior to contact with the flue gas; and or a scrubbing agent added to the recycled condensate prior to contact with the flue gas; and or a regenerator to regenerate at least a portion of the collected condensate to recover a carbon dioxide-rich stream and carbon dioxide-lean condensate for the recycling to the convection section; and or a demister to receive the scrubbed flue gas and remove entrained liquid.

Preferably, the apparatus further comprises: (in addition to the first and second heat exchanger coils) a third heat exchanger coil located downstream of the first heat exchanger in the condensing portion of the convection section for preheating the hydrocarbon: a fourth heat exchanger coil upstream of the second heat exchanger coil in the non-condensing portion of the convection section for preheating the hydrocarbon from the third heat exchanger coil: an intercooler for exchanging heat between the preheated hydrocarbon from the fourth heat exchanger coil and the preheated hydrocarbon from the third heat exchanger coil: a mixing station for combining the hydrocarbon from the fourth heat exchanger coil with the water to form the mixed feed stream for heating in the first heat exchanger coil; and a desulfurizer for desulfurizing the preheated hydrocarbon from the fourth heat exchanger coil prior to the mixing with the water. If desired, one of the first and second heat exchangers can be located in an essentially vertical convection flue section, and the other one of the first and second heat exchangers can be located in an essentially horizontal convection flue section.

Preferably, the apparatus further comprises: a fan for inducing a draft of the flue gas downstream of the second heat exchanger coil and upstream of the condensate collection and first heat exchanger coil, and discharging the flue gas downstream from the first heat exchanger into a stack; and or a diverter flue for diverting at least a portion of the flue gas, from a location that is downstream of the draft induction and upstream of the condensate collection and first heat exchanger coil, into the stack, and bypassing the condensate collection and first heat exchanger coil; and or a damper for controlling the portion of the diverted flue gas using one or more flow dampers to regulate the flow of the diverted portion and pass the flue gas downstream of the draft induction through a first portion of the stack, across the first heat exchanger coil, and then into a second portion of the stack located above the first portion, wherein at least one of the one or more dampers is located in the stack between the first and second portions of the stack.

Preferably, the apparatus further comprises an air preheat coil in the convection section and a line for supplying preheated air from the air preheat coil to a combustion burner in the radiant section.

In the foregoing embodiment or any other embodiment, the one or more process heat exchangers can generate steam, preheat boiler feed water, exchange heat with air or cooling water, or a combination thereof.

In the foregoing embodiment or any other embodiment, the CO2-lean syngas stream preferably comprises less than 0.1 vol % CO2 or is preferably essentially free of CO2.

Preferably, the absorber-stripper unit comprises a CO2 solvent, preferably an alkanolamine, more preferably methyl diethanolamine or MDEA. Desirably, the stripper is operated at a lower pressure and/or a higher temperature than the stripper.

Preferably, the methanol reactor loop operates with a carbon efficiency of equal to or greater than 95%, more preferably equal to or greater than 97%. Preferably, the carbon-lean fuel stream consists essentially of or consists of the hydrogen-rich stream from the pressure swing adsorption unit and the remaining portion of the tail gas stream.

In the foregoing embodiment or any other embodiment of the apparatus, the hydrocarbon feed stock and the remaining portion of the tail gas stream can match the fuel requirements for reforming at a rate that produces excess hydrogen to meet the firing requirements of the reformer.

Preferably, the apparatus further comprises: a condensate stripper for stripping condensate from the cooled syngas stream from the one or more process heat exchangers, and preferably a line to supply the fusel oil stream from the methanol wash unit to the condensate stripper.

For simplicity, the heat exchangers and other components are shown in the figures as being consecutively placed in the convection section of the flue. However, it is to be understood that additional components and/or other equipment and flow paths, e.g., selective catalytic reduction units, reactors, heat exchangers, and the like, may be placed upstream, in-between, and/or downstream of the components shown.

Turning to the figures in which like numerals represent like or analogous components, FIG. 1 shows a block diagram of a methanol plant 100 in accordance with embodiments of the present invention. A hydrocarbon feedstock in line 102 such as naphtha or natural gas, if not available at suitable pressure, can be compressed in compressor 104, supplied with process steam from line 106, typically in a mixed feed stream (see FIG. 2 below), and fed to steam methane reformer 108. For the purposes of simplicity and clarity, the hydrocarbon feedstock 112 is referred to hereinafter as natural gas and the reformer 108 as a steam methane reformer or SMR, by way of example and not limitation. A tail gas stream 110 can, if desired, also be introduced into the feedstock for reforming. If available at a high pressure, the tail gas can be expanded in expansion turbine 112 prior to introduction into line 114 to facilitate driving compressor 104.

Steam methane reformer 108 is fired via fuel line 116 with a low-carbon fuel such as a hydrogen rich recycle stream 118. If a hydrogen-rich stream is not available at start-up, a portion of the feedstock from line 102 can be temporarily used to fire the steam methane reformer 108 until recycle stream 118 becomes available. If desired, a purge stream 120, e.g., taken as a portion of the tail gas stream 110, can be introduced to the fuel line 116, to prevent the buildup of inerts in the process 100. In any embodiment, the fuel in line 116 comprises a carbon:hydrogen atomic ratio less than 0.5, preferably equal to or less than 0.1, more preferably equal to or less than 0.01, e.g., equal to or less than 0.008.

Figure 2:
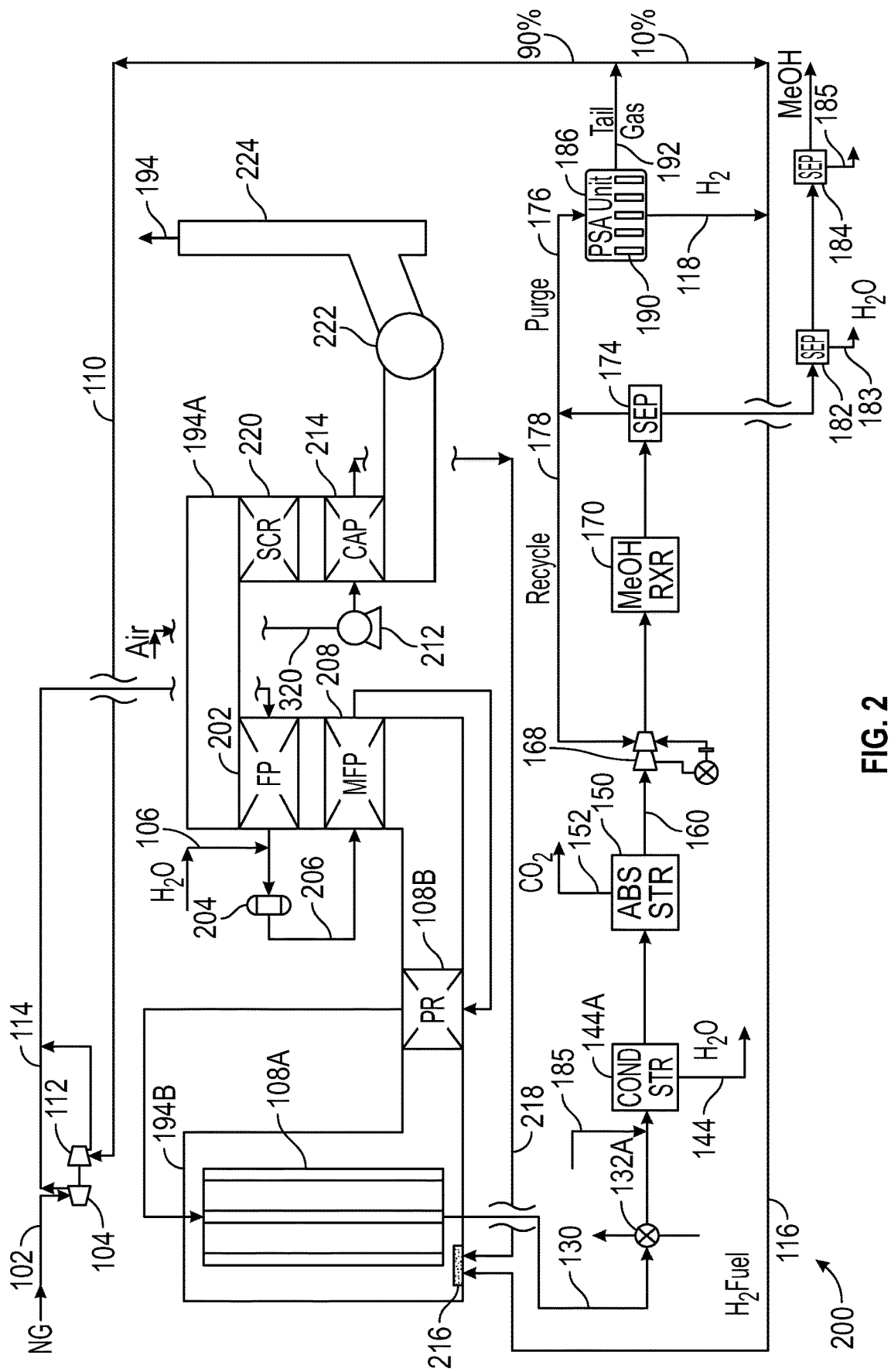
FIG. 2 is a block diagram illustrating another low-CO2 emissions methanol process and production equipment according to embodiments disclosed herein.

Steam methane reformer 108 generally includes catalyst filled tubes that are heated in a radiant section of a furnace in a manner well known to those skilled in the art. The feedstock passes internally through the tubes which are externally heated to supply the energy needed for the endothermic conversion to syngas in stream 130. In any embodiment, the combustion of the hydrogen-rich fuel provides a higher flame temperature relative to natural gas, which leads to improved firing efficiency in the reformer 108, defined as the total SMR duty divided by the total SMR firing, e.g., an efficiency of at least 94%, e.g., 94.17%. For example, the SMR 108 can operate with a crossover temperature (xot) of 538-649° C. (1000-1200° F.), e.g., 566° C. (1050° F.), and a reformer exit temperature (rcot) of 816-916° C. (1500-1680° F.), e.g., 902° C. (1655° F.). Since the pre-reformed feed contains more hydrogen and less hydrocarbon heavier than methane, the xot can be shifted to a higher temperature (about 28° C. (50° F.) higher) without concern for cracking, i.e., a conventionally natural gas fired SMR generally has a typical xot range of just 510-621° C. (950-1150° F.). In a preferred embodiment, the xot can be greater than 621° C. (1150° F.), e.g., greater than 621° C. (1150° F.) up to 649° C. (1200° F.). Steam methane reformer 108 can, if desired, include one or more reforming exchangers, e.g., pre-reformers, as shown in FIG. 2 discussed below.

If desired, SMR reformer 108 can optionally include shift converters (not shown) such as a high temperature shift converter and a low temperature shift converter, which react CO and H2O to make more hydrogen and CO2, but preferably does not include shift conversion reactors so that the CO2 concentration is kept low. For methanol plants, the synthesis gas preferably has a molar ratio of hydrogen to CO in the range of 2-6, more preferably 3-5.

Syngas stream 130 from SMR 108 comprises a mixture of primarily hydrogen, carbon monoxide, and carbon dioxide, with lesser amounts of inerts such as nitrogen and argon and unreacted hydrocarbons such as methane. The stream 130 is cooled in exchangers 132, 134, 136 to generate steam in line 138 at 316° C. (600° F.) for example, to preheat boiler feed water to 177° C. (350° F.) for example in line 140, and by air cooling or cooling water exchange via line 142 at 40° C. (104° F.) for example. Process condensate is recovered from condensate stripper 144A in line 144.

The dried synthesis gas in stream 146 is then passed through a CO2 removal system 150 to recover CO2 product stream 152. The CO2 can be removed, for example, by adsorption, absorption, cryogenically, using membranes and the like. The CO2 removal system preferably comprises an absorber-stripper using a solvent such as alkanolamines like MEA, DEA, MDEA, and so forth, soda-lime, pyrimidinylamino compounds such as 2-(pyrimidin-2-ylamino)acetic acid, 3-(pyrimidin-2-ylamino)propanoic acid, 4-(pyrimidin-2-ylamino)butanoic acid, and so forth, and the like. Amine scrubbing of CO2 is particularly effective at the higher pressure of the synthesis gas 146 relative to the lower pressure of flue gas. Typically, the absorber 154 is operated at, for example, about 1.86 MPa (270) psig) and about 38° C. (100° F.). In any embodiment, the CO2 removal system 150 can include absorption column 154 and stripper column 156. In absorption column 154, the synthesis gas is contacted with the solvent from stream 158 and CO2 is absorbed. CO2-lean synthesis gas stream 160 is obtained overhead. CO2-rich absorbent is collected as a bottoms stream 162 and supplied to stripper 156 where it is heated by means of reboiler 164 to obtain CO2 product stream 152 overhead, and CO2-lean solvent stream 158 as a bottoms product. The stripper 156 can also be operated at a lower pressure than the absorber 154.

The pressure of the CO2-lean make-up synthesis gas stream 160 is increased in compressor 168 and recirculated with unreacted syngas recycle 178 through methanol synthesis reactor 170. The methanol synthesis reactor 170 can operate at a higher pressure than the reformer 108, generally comprises a catalyst, and operates with a carbon efficiency of at least 95%, e.g., 97 or 97.3%. Unreacted syngas stream 172 is recovered from methanol separator 174. A portion is supplied in stream 176 as a purge to PSA unit 180, and the remainder is recycled via line 178 to compressor 168. Methanol stream 180 is recovered after methanol wash column 182 removes condensate stream 183 and finishing column 184 recovers fusel oil stream 185. Fusel oil 185 recovered from finishing column 184 can, if desired, be recycled to the condensate stripper 144A, in contrast to the prior art where the fusel oil is typically burned to fire the primary reformer 108A via dedicated burners specially designed for this purpose.

PSA unit 186 is a pressure swing adsorption unit known to those skilled in the art that collects hydrogen in one or more adsorbent beds 190. The hydrogen 191 is released from the beds 190 during a regeneration cycle at a lower pressure to obtain an essentially pure hydrogen stream 118, which is supplied as the main fuel in line 116 to SMR 108. A PSA tail gas stream 192 comprised predominantly of non-hydrogen species is obtained at pressure downstream from the beds 188, and the majority is expanded in turboexpander 118 and supplied with the feedstock to the SMR 108 in line 114. The remaining portion is purged in line 120 to fuel stream 116 to prevent inerts from building up in the process 100, as discussed above. The purge stream 120 supplies a small amount of carbon which produces a small amount of CO2 in flue gas stream 194.

FIG. 2 is a block diagram in accordance with embodiments of the present invention similar to FIG. 1 but showing the process 200 in which the generic reformer 108 is replaced with a primary reformer 108A and a pre-reformer 108B, and also showing the details of an embodiment of the flue gas convection section 194A. The primary reformer catalyst is typically 12-15% nickel, whereas the pre-reformer catalyst can comprise up to about 40 wt % nickel, or it may use the same catalyst as the primary reformer.

In the FIG. 2 embodiments, the feed stream 114 is passed through feed preheat exchanger 202 disposed in the convection section 194A, where it is heated in indirect heat exchange with the flue gas 194, passed through desulfurizer 204, and then mixed with water or steam from line 106A. The mixed feed stream 206 is then heated in mixed feed preheater 208, located in the convection section 194A upstream from the feed preheater 202 with respect to the flue gas 194 flow, and thence passed through pre-reformer 108B, which is configured as a pre-reformer comprised of catalyst-filled tubes, preferably disposed in a hottest part of the convection section 194A just downstream from the radiant section 194B. If desired, the pre-reformer 108B could alternatively receive the effluent from the primary reformer 108A as a post-primary reformer.

Air from intake line 210 can be conveyed by forced draft fan 212 through cold air preheater 214 disposed in convection section 194A downstream from feed preheater 202, and then to a burner 216 via line 218 for combustion of carbon-lean fuel stream 116 as discussed above in connection with FIG. 1.

Convection section 194A can, if desired, include a selective catalytic reduction unit 220, preferably disposed upstream from cold air preheater 214, to convert NOx to nitrogen. Induced draft fan 222 downstream from the cold air preheater 214 can force flue gas 194 from convection section 194A and into discharge stack 224.

Synthesis gas stream 130 can be processed as described above in connection with FIG. 1, i.e., cooling in one or more heat exchangers in heat exchange section 132A, separating process condensate 144 via condensate stripper 144A, CO2 removal from unit 150, compression in compressor 168, methanol synthesis in reactor 170, crude methanol recovery from wash column 174, and recycle via line 178. Also as described in connection with FIG. 1. PSA unit 186 receives a purge stream 176 from recycle line 178 and produces hydrogen stream 118, which is supplied in its entirety to burner 216, and tail gas stream 192, which is predominantly supplied (e.g., 90% or more) to the hydrocarbon feed line 114 and a minor amount (e.g., 10% or less) of which is purged to the fuel line 116.

Figure 3:
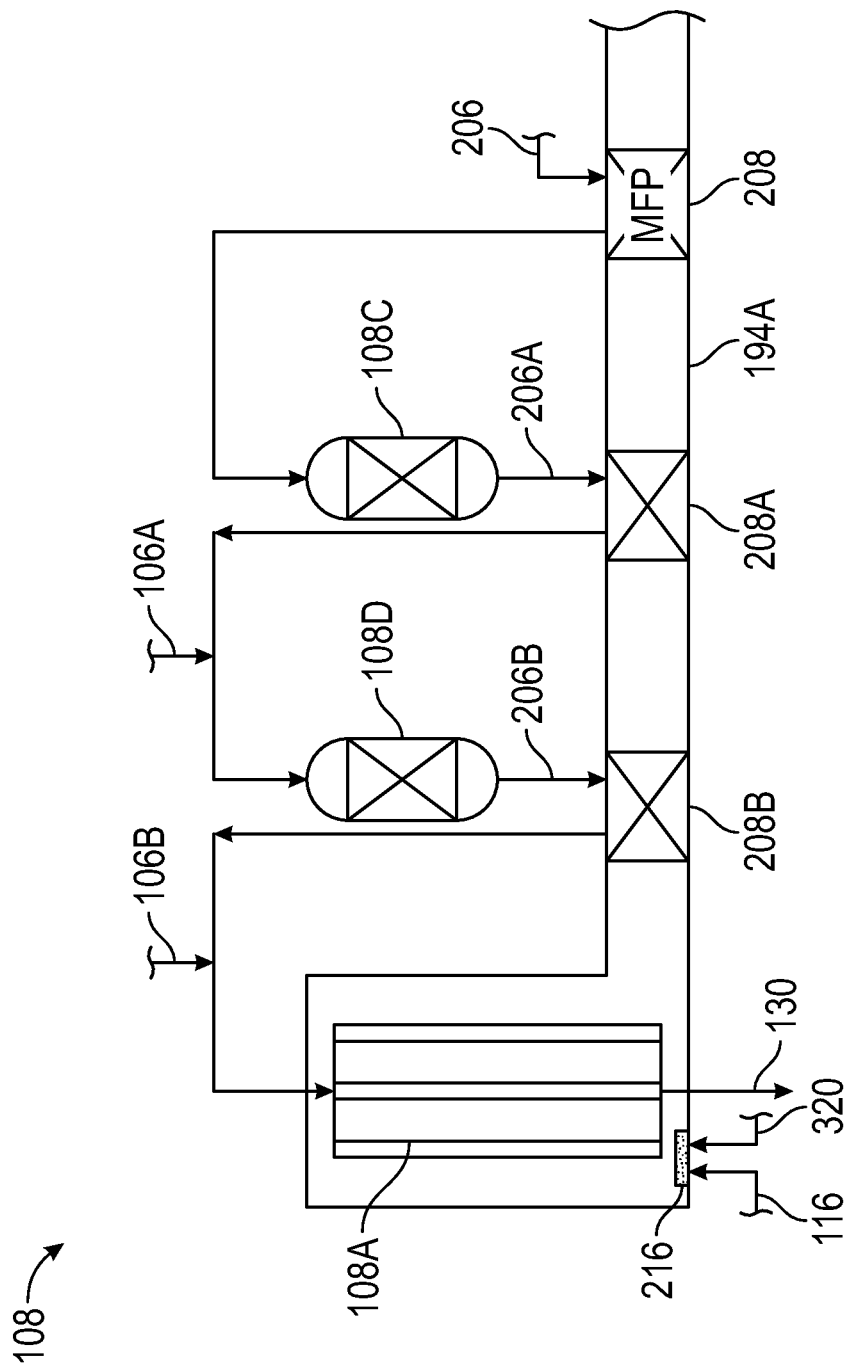
FIG. 3 is a block diagram illustrating a reformer with two pre-reformers according to embodiments disclosed herein.

FIG. 3 shows an alternate arrangement of the reformer 108 comprising primary steam methane reformer 108A, and first and second catalytic pre-reformers 108C, 108D. The pre-reformers 108C, 108D are both shown placed externally with respect to the convection section 194A, although they could, if desired, be positioned within the convection section 194A as shown in FIG. 2. Steam from line 106A is added to form mixed feed stream 206 which is supplied to preheater 208 in the convection section. Preheated mixed feed stream 206 from convection section preheater 208 is supplied to pre-reformer 108C, typically at a temperature of about 482-538° C. (900-1000° F.), where it is partially reformed and recovered in stream 206A, typically at a temperature of about 454-510° C. (850-950° F.). The first partially reformed stream 206A can then be optionally mixed with supplemental steam from line 106B, re-heated to about 566-677° C. (1050-1250° F.) in exchanger 208A, and thence passed through second pre-reformer 108D. A second partially reformed stream 206B (e.g., at 538-621° C. (1000-1150° F.)) with a higher syngas content is recovered from the second pre-reformer 108D, optionally supplemented with steam addition in line 106C, re-heated in exchanger 208B (e.g., to 538-649° C. (1000-1200° F.)), and thence supplied to the primary reformer 108A as described above.

Figure 4:
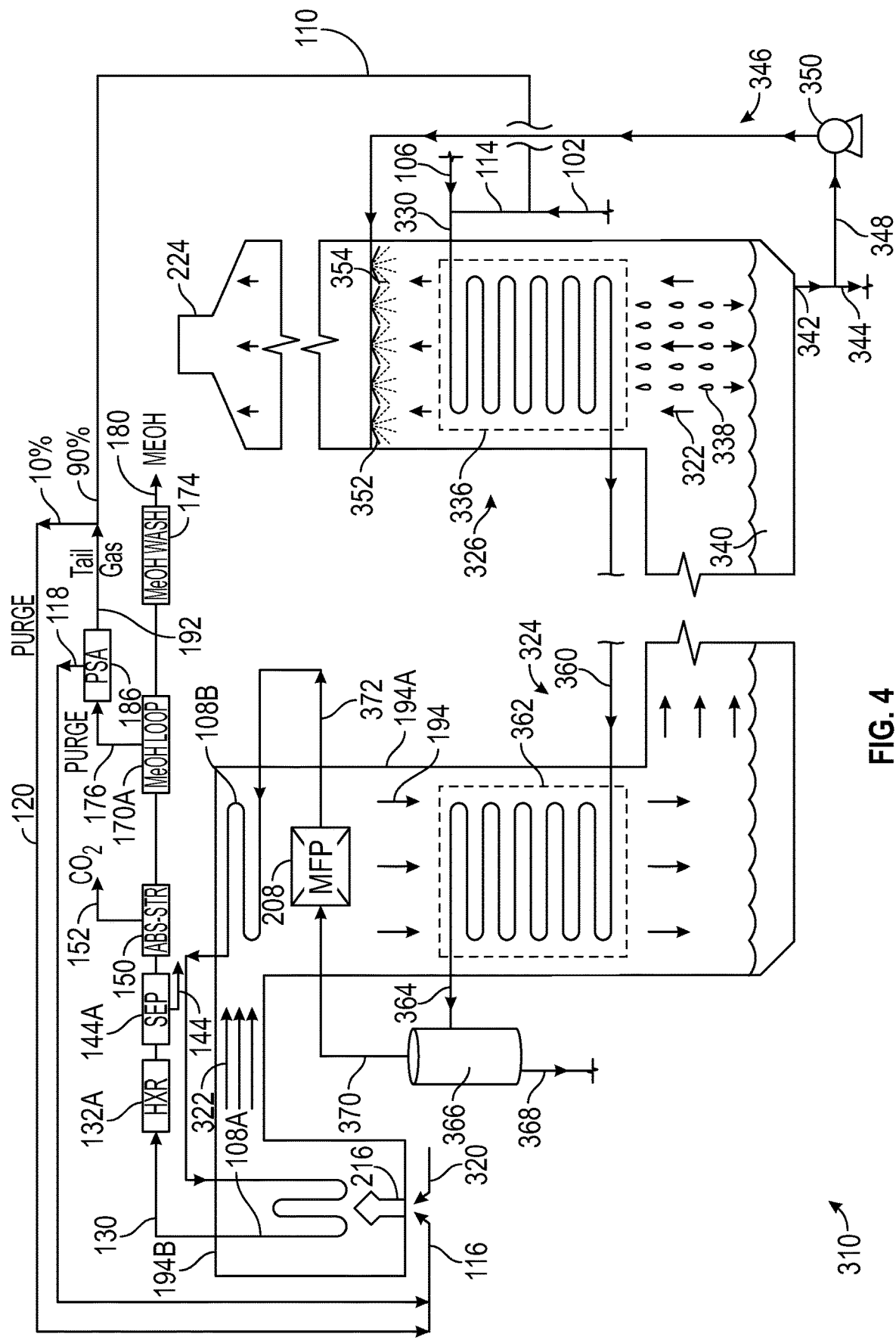
FIG. 4 is a block diagram illustrating a fired heater having a condensing convection section according to embodiments disclosed herein.

FIG. 4 is a block diagram in accordance with embodiments of the present invention illustrating a convection section 194A comprised of a non-condensing convection section 324, and condensing convection section 326. Similarly as described in connection with FIG. 2 above, a radiant section 194B has a burner 216 receiving fuel from line 116 and oxidant from line 320 to heat primary reformer 108A in radiant section 194B. Synthesis gas stream 130 can be processed as described above in connection with FIG. 1, i.e., cooling in one or more heat exchangers in heat exchange section 132A, separating process condensate 144 via separator 144A, CO2 152 removal from absorber-stripper unit 150, methanol synthesis in methanol synthesis loop 170A, and methanol 180 recovery from wash column 174. Also as described in connection with FIGS. 1-2, PSA unit 186 receives a purge stream 176 from methanol synthesis loop 170A and produces hydrogen stream 118, which is supplied in its entirety to burner 216, and tail gas stream 192, which is predominantly supplied to the hydrocarbon feed line 114 and a minor amount of which is purged to the fuel line 116.

Flue gas 194 passes from the radiant section 194B, through non-condensing convection section 324, condensing convection section 326, end exits from stack 224. Since it is the product of combustion of low-carbon, sulfur-free fuel 116, and may also be free of sulfur oxides in the event the feed gas 114 is preferably desulfurized, the flue gas 194 has a low acid content and can form a low-acid condensate, facilitating operation of the condensing convection section 326.

A process fluid stream 330, comprising natural gas (which is preferably desulfurized) from line 102 and or water from line 106, flows through first heat exchanger 336, e.g., a condensing coil, in the condensing convection section 326 in heat exchange relationship with the flue gas 194 condensing on the outside surface of the condensing coil. Process fluid stream 330 enters the first heat exchanger 336 at a temperature that may be below the dew point of the flue gas 194. When present, the relatively high heat capacity of water 106 in the process fluid 330 allows for improved removal of heat compared to using the hydrocarbon fluid 332 alone. In embodiments, the first heat exchanger 336 has sufficient surface area and contact with the flue gas 194 such that the temperature of the flue gas is reduced to its dew point or below. Condensate 338, which forms on the coil of the first heat exchanger 36, falls by gravity through the flue gas 194 flowing upwardly at a velocity less than the terminal velocity of the condensate droplets collected below in a collection zone, e.g., basin 340 located beneath the first heat exchanger 336.

In embodiments, the basin 340 comprises at least one take-off or drain 342, through which condensate 338 can be removed, e.g., via a condensate blowdown line 344 or the like. If desired, some or all of condensate 338 may be recycled back into contact with the flue gas 194 via condensate recycle loop 346 having a recycle line 348, pump 350, and distributor 352 located above and/or downstream from and/or in close proximity to the first heat exchanger 336, e.g., the distributor 352 may be located such that the recycled condensate impinges on or otherwise contacts the first heat exchanger 336, such as by locating spray nozzles 54 between rows of the condensing coils. In embodiments, the distributor 352 may be a spray bar comprising one or more spray nozzles 354 and/or other atomization devices, including, for example, gas assisted atomization devices, drip bars having one or more liquid outlets, and the like for contacting and further cooling and/or scrubbing flue gas 194, which then flows out through the stack 224.

Figure 5:
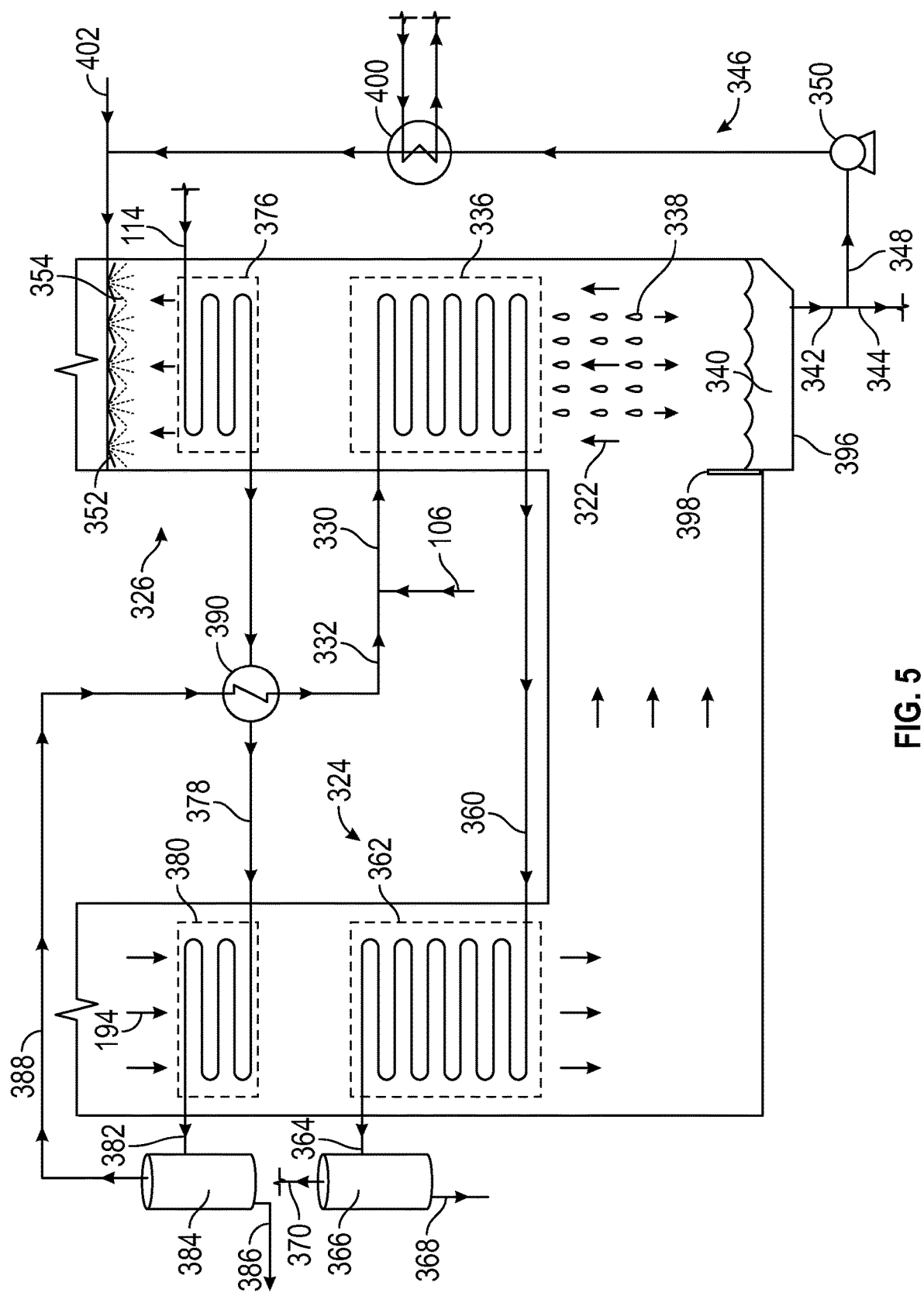
FIG. 5 is a block diagram illustrating feed gas desulfurization according to embodiments disclosed herein.

If desired, exposed surfaces in the condensing convection section 326, such as the walls and tubes of the heat exchangers, e.g., first heat exchanger 336 and third heat exchanger 376 (see. FIG. 5), may be coated and/or constructed of a corrosion-resistant material for protection from acidic flue gas or condensate and/or caustic scrubbing agents. In embodiments, one or more surfaces located in the condensing convection section 326 comprise at least a layer of corrosion resistant material, such as, for example, ceramics (titania, alumina, silica, etc.); nickel chrome, aluminum, tungsten, HASTELLOY®; alloy, molybdenum, stainless steel, chromium carbide, bronze, brass, STELLITE®; cobalt-chromium alloy, zinc, titanium, metal nitrides, and other superalloys: polymer coatings such as xylan, fluorocarbons, fluoropolymers, silicones, epoxies, perfluoropolyethylene (e.g., TEFLON® industrial coating), DUPONT® FEP (fluorinated ethylene propylene), PFA (perfluoroalkoxy alkane), PTFE (polytetrafluoroethylene), HALAR® ECTFE (ethylene and chlorotrifluoroethylene), TEFZEL® ETFE (ethylene tetrafluoroethylene), nylon such as Nylon 11, or the like: or combinations. The exposed surfaces of these components may be coated or clad with the corrosion-resistant material and/or the components may be formed from (consist of or consist essentially of) the corrosion-resistant material. Various forging, casting, molding, drawing, stamping, machining, and other component fabrication technologies are available. Various coating technologies are also known to those skilled in the art, e.g., airless spraying, combustion wire process, electrostatic deposition, chemical vapor deposition, physical vapor deposition, high velocity oxygen fuel, liquid dispersion, plasma, plural spray, powder metallizing, wire arc process, nanocoating, and the like.

As shown in FIG. 4, process fluid stream 360 flows from the first heat exchanger 336 and into second heat exchanger 362 in the upstream, non-condensing convection section 324 in heat exchange relationship to cool the flue gas 194. The heated, exiting process fluid stream 364 from the second heat exchanger 362 may then be further processed and/or supplied to the reactor tubes 108A. In embodiments, process fluid stream 364 comprises hot vapor, e.g., hydrocarbon (preferably methane) gas and superheated steam, or hydrocarbon gas and liquid and/or steam and water, and/or may, if desired, be directed into a saturator vessel 366, e.g., a saturator drum. The saturator vessel 366 may allow any separated solids and/or remaining liquid to exit via saturator blowdown 368, and the hydrocarbon gas and any other vapor phase components, such as steam, exit via vapor line 370, which is mixed with steam from line 106A and supplied to the mixed feed preheater 208 located upstream in convection section 194A. Pre-heated mixed feed exits MFP 208 in line 372, is then supplied to pre-reformer tubes 108B located upstream in convection heat exchange relationship with the flue gas 194 directly from radiant section 194B, and thence to reactor tubes 108A.

In other embodiments of the non-condensing convection section 324 and condensing convection section 326, FIG. 5 shows the FIG. 4 process with feed gas desulfurization and various condensate recirculation embodiments. Any or all of the features shown in FIGS. 1-4 may be present in FIG. 5, and vice versa, although some components are omitted for enhanced clarity. In the embodiment of FIG. 5, the hydrocarbon process fluid stream 114 is first supplied to a third heat exchanger 376, e.g., a condensing preheat coil, which may be located in heat exchange relationship with the flue gas 194 in the condensing convection section 326, e.g., downstream of the first heat exchanger 336. If desired, the stream 114 may be available at a lower temperature than in FIG. 4, e.g., at ambient temperature or pre-chilled, and the use of the third heat exchanger 376 can allow the additional extraction of additional heat at relatively lower temperatures.

In embodiments, the exiting hydrocarbon fluid from the third heat exchanger 376 is then directed via line 378 into a fourth heat exchanger 380, which may be located in heat exchange relationship with the flue gas 194 in the non-condensing convection section 324, e.g., upstream of the second heat exchanger 362. The hydrocarbon flowing from the fourth heat exchanger 380 in line 382 comprises vapor, and preferably consists of or consists essentially of vapor, i.e., is sufficiently free of solids and/or liquids to allow processing in the downstream treatment unit(s) 384, e.g., a desulfurizer unit. A sulfur-containing waste stream 386 may be discharged continuously or periodically from treatment unit 384. If desired, the hydrocarbon fluid stream 388 from the treatment unit 384 may be passed through an interchanger 390, in heat exchange relationship with the hydrocarbon in stream in line 378 for cooling, and may then be combined with water via stream 106 as in FIG. 1 for supply to the first heat exchanger 336. In this manner, heat that may be required for any desulfurization and/or other treatment of the hydrocarbon feed stream 102 is conveniently extracted from the non-condensing convection section 324.

FIG. 5 also shows additional and/or alternative embodiments for the condensate recirculation system 346. In these embodiments, the basin 340 may be of any suitable length, width, depth, and the like, located in a well or depression 396 that may be defined wholly or in part by a weir or dam 398. The system 346 may further include heat exchanger 400 to reduce the temperature of the recycled condensate in line 348 supplied to distributor 352, which may be positioned above the first and or third heat exchangers 336, 376 and/or in close proximity thereto.

In embodiments, the system 346 may further include scrubbing agent addition into the recycled condensate via line 402. In embodiments, the scrubbing agent may be added as a solution, e.g., an aqueous solution, preferably of an amine compound, i.e., R—NR$^1$R$^2$, wherein R is alkyl or alkanol having from 1 to 40 carbon atoms, preferably from 1 to 12 carbon atoms; and R$^1$ and R$^2$ are independently selected from hydrogen and alkyl or alkanol having from 1 to 40) carbon atoms, preferably from 1 to 12 carbon atoms. The preferred amine scrubbing agent is MDEA or monoethanolamine: various other amines are known in the art to improve the sorptive scrubbing ability of condensate and other aqueous solutions.

Figure 6:
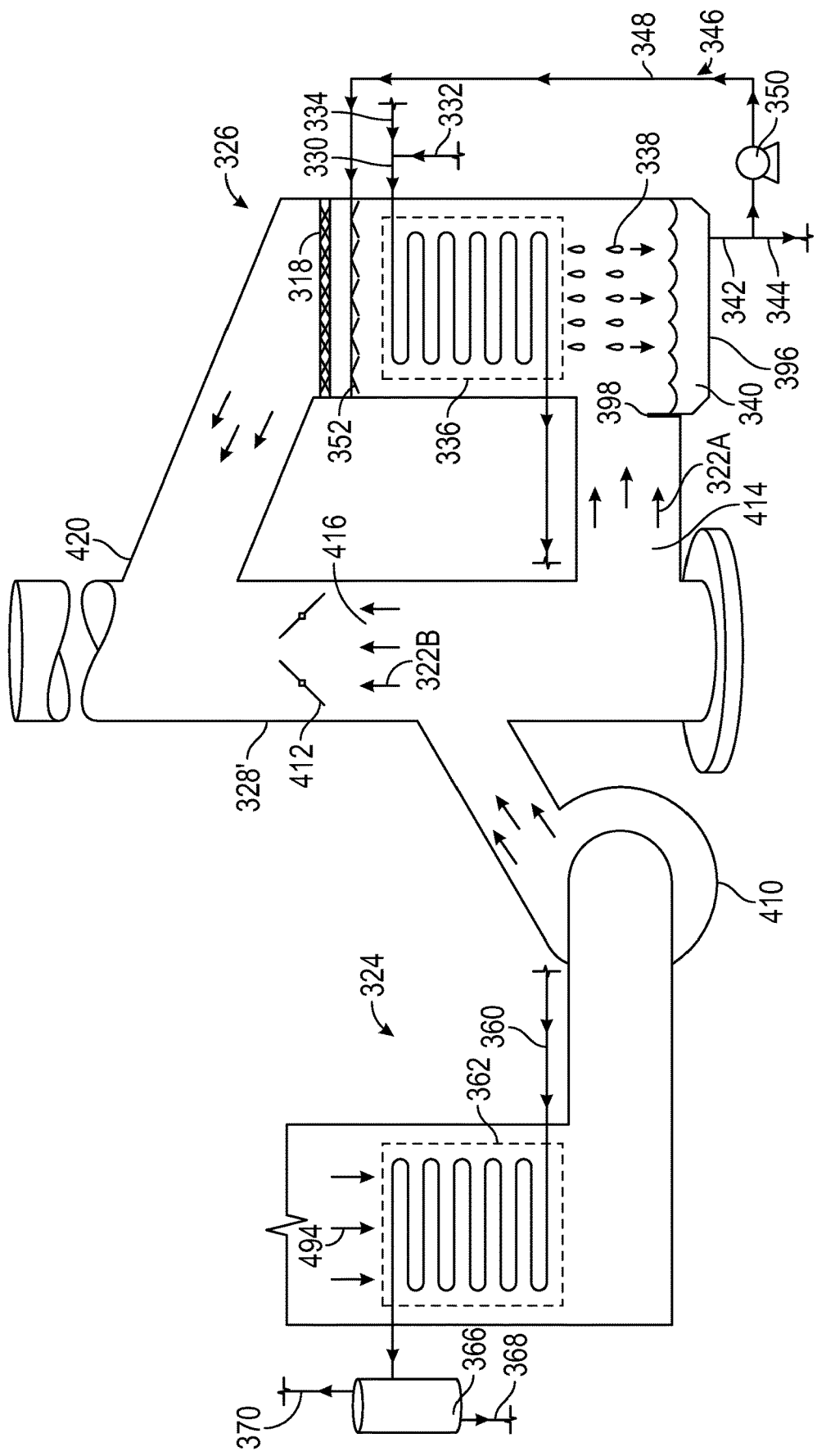
FIG. 6 is a block diagram illustrating flue gas bypass according to embodiments disclosed herein.

In another embodiment, FIG. 6 shows the process of FIGS. 1-5 with a split flue or flue gas bypass. Any or all of the features shown in FIGS. 1-5 may be present in FIG. 6, and vice versa, although some components are omitted for enhanced clarity. In the embodiment of FIG. 6, the hot flue gas 194 flows across the second heat exchanger 362 disposed in the non-condensing convection section 324, and if needed, is drawn through induced draft fan 410 into stack 328'. One or more dampers 412 control the proportion of flue gas 322A flowing to flow path 414 into the condensing convection section 326 to the first heat exchanger 336, and the proportion of flue gas 322B flowing directly out of the stack 328', bypassing the condensing convection section 326 via flow path 416. The flue gas 322A flows through the first heat exchanger 336, distributor 352, and demister 418, and then reenters the stack 328' at the ducting joint 420 above the dampers 412, where it is recombined with the flue gas 322B for discharge. This embodiment allows bypassing the condensing section 326, allowing relatively higher flue gas temperature operation, whether expected or unexpected, and can be used to prevent damage to corrosion resistant materials or coatings. For example, in the event of a process excursion due to a loss of cooling fluid to the condensing section 326, flue gas temperature could rise to a point which damages equipment, e.g., polymer protective coatings may melt. By controlling the dampers 412, this damage may be avoided.

As shown in FIG. 6, the demister 418 may be located downstream of the first heat exchanger 336 and or distributor 352 to inhibit condensate entrainment to the stack 328".

Figure 7:
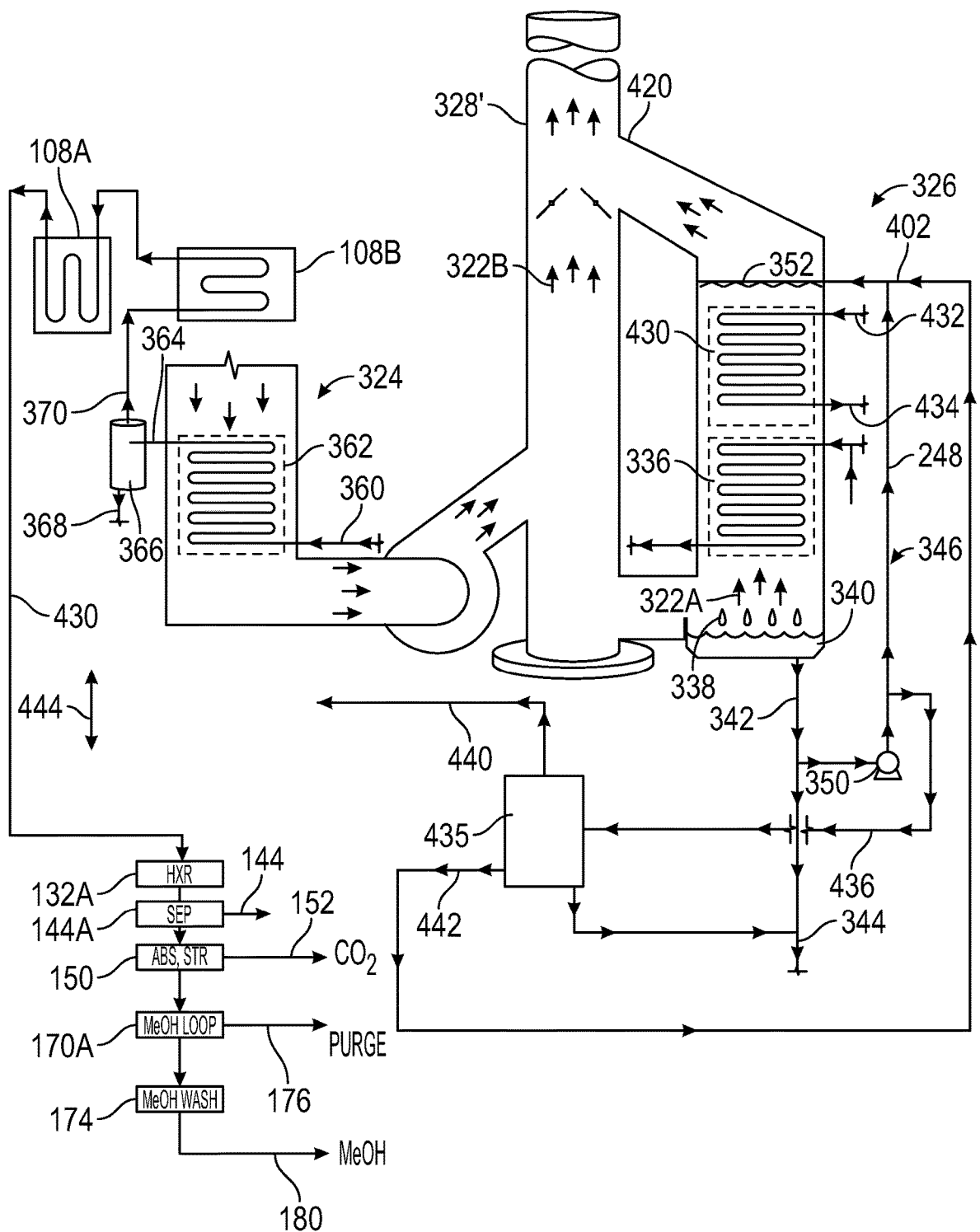
FIG. 7 is a block diagram illustrating a regenerative scrubbing system in a condensing convection section according to embodiments disclosed herein.

In another embodiment, FIG. 7 shows the process of FIGS. 1-6 with an additional heat exchanger in the convection section and scrubbing agent regeneration. Any or all of the features shown in FIGS. 1-6 may be present in FIG. 7, and vice versa, although some components are omitted for enhanced clarity. In the embodiment of FIG. 7, an additional heat exchanger(s) 430, which may the third heat exchanger 376 (FIG. 5) and/or another heat exchanger in lieu of or in addition to third heat exchanger 376, is located in the condensing convection section 326, e.g., downstream of first heat exchanger 336 and/or upstream of distributor 352. The cooling fluid 432 supplied to the heat exchanger 430 may be air which is preheated and recovered in line 434, e.g., before being supplied as combustion air for the burners 216 via line 218 (see FIGS. 4-5). In other embodiments, the fluid 432 may be used to transfer heat to and from other parts of the process associated with the fired heater 108A (FIGS. 2-4), or to or from another process.

In FIG. 7, the scrubbing agent 402 may comprise an amine solution as discussed above to improve scrubbing of carbon dioxide ($CO_2$) from the flue gas 322A. In embodiments, at least a portion of the condensate/scrubbing solution from line 342 is directed via line 436 to regenerator 438 where it is treated to remove $CO_2$, according to principles well known in the art, recovering a carbon-dioxide-rich stream 440, and a regenerated, aqueous carbon dioxide-lean stream 442. The scrubbing agent in the regenerated stream 442 may then be supplied to the recycled condensate via line 402. Blowdown from the regenerator may be supplied to line 344 for appropriate treatment.

Figure 8:
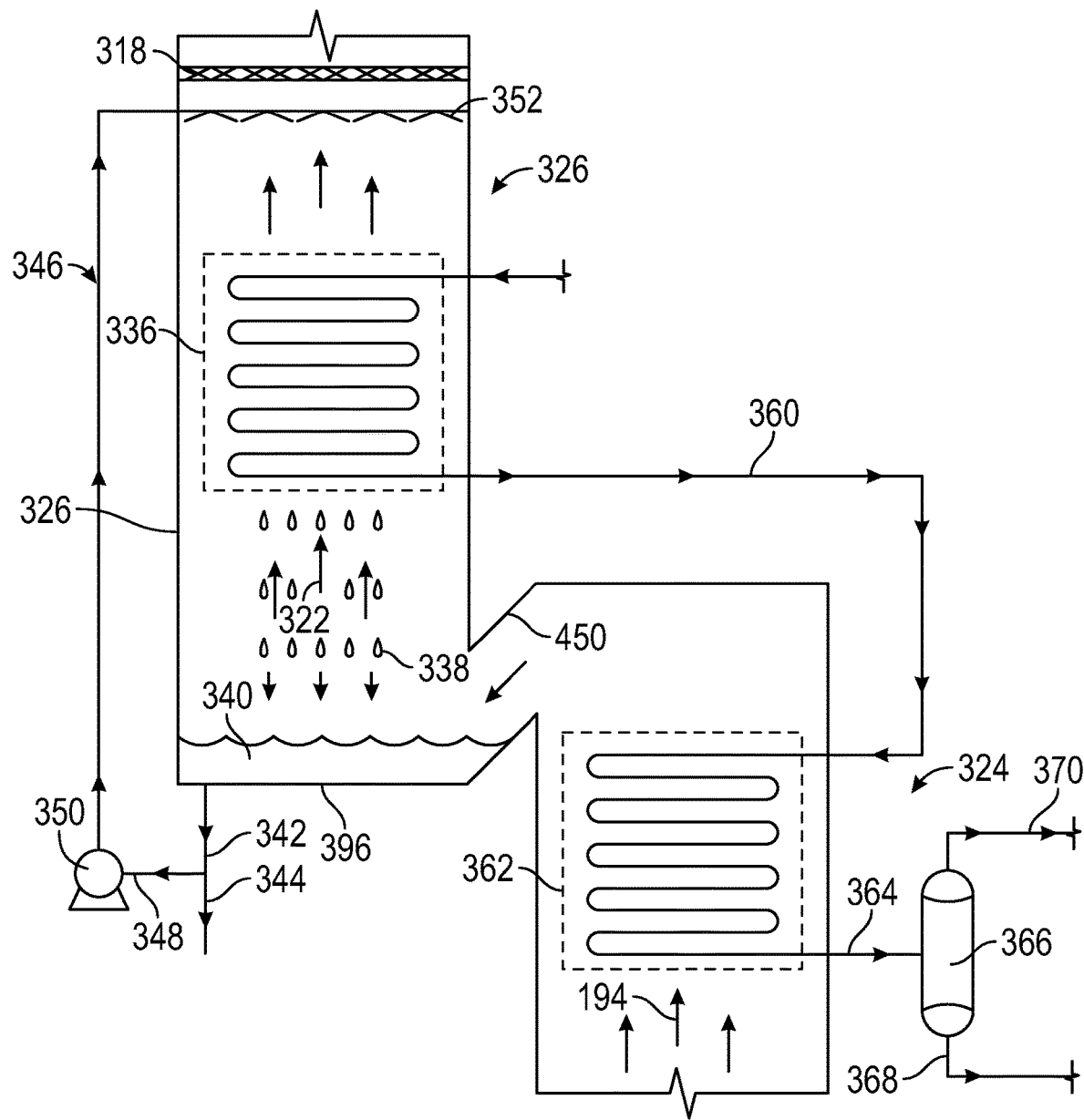
FIG. 8 is a block diagram illustrating an upflow convection section according to embodiments disclosed herein.

In another embodiment, FIG. 8 shows the process of FIGS. 1-7 with upflow vertical non-condensing and condensing convection sections. Any or all of the features shown in FIGS. 1-6 may be present in FIG. 8, and vice versa, although some components are omitted for enhanced clarity. In the embodiment of FIG. 8, both of the condensing convection section 326 and the noncondensing convection section 324 are generally vertical with relatively minor horizontal flue gas flow. A variety of fired heaters have designs using a noncondensing convection section 324 generally configured in a vertical orientation. Examples where the noncondensing convection section 324 is desirably vertical include various steam methane reformers, steam crackers, and the like.

In FIG. 8, the flue gas 194 flows upwardly through the second heat exchanger 362, and then flows slightly downwardly through offset 450, which provides downwardly sloped walls for any condensate to drain by gravity into the basin 340 in well 396, and inhibits the condensate 338 from falling into the noncondensing convection section 324. The flue gas 194 then flows upwardly through the first heat exchanger 336 and recirculation loop 346 returns the condensate to distributor 354, as described above in any of FIGS. 4-7.

Figure 9:
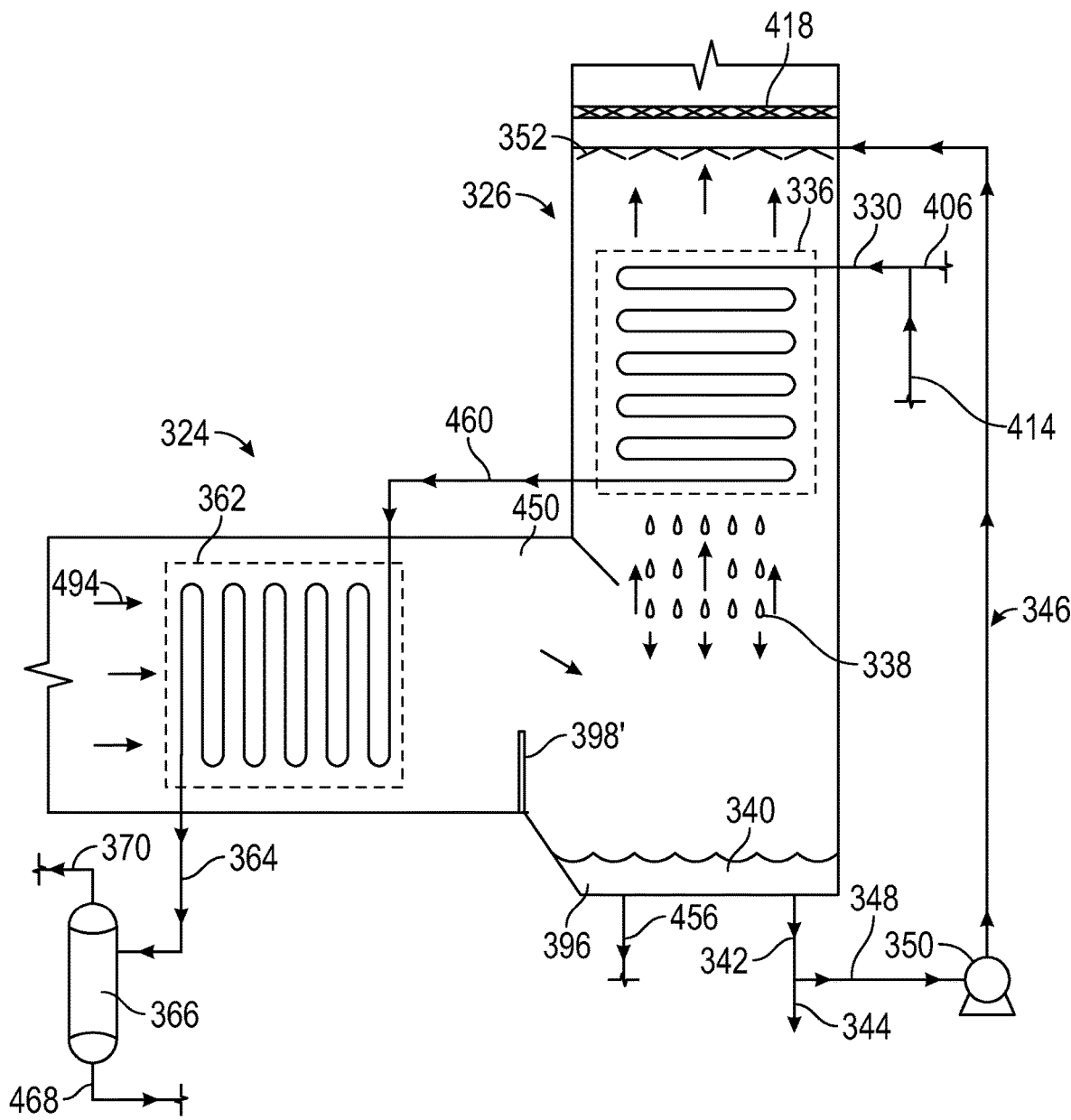
FIG. 9 is a block diagram illustrating a scrubbing system with both horizontal and vertical heat exchange zones in a convection section according to embodiments disclosed herein.

In another embodiment, FIG. 9 shows the process of FIGS. 1-7 with a generally horizontal non-condensing convection section 324 and a generally vertical condensing convection section 326. Any or all of the features shown in FIGS. 1-8 may be present in FIG. 9, and vice versa, although some components are omitted for enhanced clarity. Fired heaters may have designs using a noncondensing convection section 324 generally configured in a horizontal orientation.

In FIG. 9, the flue gas 194 flows generally horizontally through the second heat exchanger 362, and then flows slightly downwardly through offset 450, which provides downwardly sloped walls for any condensate to drain by gravity into the basin 340 in well 396, and inhibits the condensate 338 from falling into or otherwise entering the noncondensing convection section 324. The offset 450 may also include at its entry a dam 398' that is sufficiently high to increase the velocity of the flue gas 322 and further inhibit entry of the condensate into the noncondensing convection section 324. The flue gas 194 then flows upwardly through the first heat exchanger 336 and recirculation loop 346 returns the condensate to distributor 354, as described above in any of FIGS. 2-6. If desired, the basin 340 may be equipped with drain 456 that may be separate from drain 344 in recirculation system 346, e.g., to provide another way of removing condensate in the event there is an unexpected accumulation in the basin 340 that might overflow the dam 398'.

EMBODIMENTS LISTING

Accordingly, in some aspects the disclosure herein relates generally to methods and apparatus for improved fired heaters according to the following embodiments, among others:

1. A low-CO2 emission methanol process, comprising the steps of:
   a) mixing a hydrocarbon feed stock with water to form a mixed feed stream;
   b) reforming the mixed feed stream in a reforming furnace comprising a radiant section and a convection section to form a syngas stream;
   c) supplying air and a carbon-lean fuel stream comprising hydrogen to fire the radiant section;
   d) passing flue gas from the radiant section to the convection section:
   e) cooling the flue gas in the convection section and optionally removing particulates from the flue gas;
   f) discharging the cooled flue gas, wherein the flue gas is lean in CO2 (preferably less than 3 vol %, more preferably less than 1.5 vol %, and even more preferably less than 1 vol %, dry basis);
   g) cooling the syngas stream;
   h) passing the cooled syngas stream directly to an absorber-stripper unit to produce a CO2 rich stream and a CO2-lean syngas stream;
   i) compressing and passing the CO2-lean syngas stream to a methanol reactor loop to produce a methanol-rich stream, wherein the methanol reactor loop comprises a methanol synthesis reactor, a methanol recovery section to recover a crude methanol stream and a recycle syngas stream, and a recycle compressor to compress the recycle syngas stream to a pressure of the reactor, wherein the pressure of the reactor is higher than a pressure of the mixed feed stream in step (b);
   j) processing the crude methanol stream in a methanol wash unit to recover a methanol product, a condensate stream, and a fusel oil stream;
   k) supplying a purge stream from the methanol reactor loop to a pressure swing adsorption unit to obtain a hydrogen-rich stream and a hydrogen-lean tail gas stream:
   l) supplying the hydrogen-rich stream to the carbon-lean fuel stream in step (c); m) supplying at least a portion (preferably 90% or more) of the tail gas stream from step (k) to the hydrocarbon feed stock in step (a);
   n) purging a remaining portion (preferably 10% or less) of the tail gas stream from step (m) to the carbon-lean fuel stream in step (c).

2. The low-CO2 emission methanol process of embodiment 1, wherein the hydrocarbon feed stock comprises natural gas and wherein the mixed feed stream preferably comprises a molar ratio of steam to carbon from 1 to 5, more preferably from 1.8 to 2.5.

3. The low-CO2 emission methanol process of embodiment 1 or embodiment 2, wherein the reforming step (b) comprises:
   b-1) pre-reforming the mixed feed stream to form a partially reformed feed stream; and
   b-2) primary reforming of the partially reformed feed stream in the radiant section of the reformer.

4. The low-CO2 emission methanol process of any preceding embodiment, wherein the reforming step (b) comprises:
   B-1) supplying the mixed feed stream to a first pre-reformer to form a first partially reformed feed stream;
   B-2) supplying the first partially reformed feed stream to a second pre-reformer to form a second partially reformed feed stream;

B-3) passing the second partially reformed feed stream to the radiant section of the reforming furnace to produce the syngas stream.

5. The low-CO2 emission methanol process of any preceding embodiment wherein the pre-reforming is in one or more pre-reformers disposed externally of the convection section and receiving the mixed feed stream from a coil disposed in the convection section.

6. The low-CO2 emission methanol process of any preceding embodiment wherein the pre-reforming is in one or more pre-reformers disposed in the convection section in heat exchange relationship with the flue gas from the radiant section.

7. The low-CO2 emission methanol process of any preceding embodiment, wherein the reforming step has an efficiency of at least 90%, preferably at least 92%, and more preferably at least 94%.

8. The low-CO2 emission methanol process of any preceding embodiment, wherein the reforming step (b) comprises a crossover temperature of 566° C. (1050° F.) or less and a reformer outlet temperature of at least 902° C. (1655° F.).

9. The low-CO2 emission methanol process of any preceding embodiment, wherein a ratio of air to fuel in step (c) produces a flame temperature equal to or greater than 2500° K.

10. The low-CO2 emission methanol process of any preceding embodiment, further comprising the steps of:
    e-1) pre-heating the hydrocarbon feed stock in a first heat exchanger coil in the convection section;
    e-2) wherein the mixing in step (a) comprises saturating the pre-heated hydrocarbon feed stock from step (e-1);
    e-3) heating the mixed feed stream from step (e-2) with the flue gas in a second heat exchanger coil in the convection section upstream of the first heat exchanger coil with respect to flue gas flow through the convection section, to superheat the mixed feed stream;
    e-4) pre-reforming the superheated mixed feed stream in one or more pre-reformers disposed in heat exchange relationship with the flue gas in the convection section upstream of the second heat exchanger coil with respect to flue gas flow to form a partially reformed stream;
    e-5) optionally pre-heating the pre-reformed stream, in a third heat exchanger coil in the convection section upstream of the one or more pre-reformers with respect to flue gas flow through the convection section; and
    b-2) reforming the partially reformed feed stream in the radiant section.

11. The low-CO2 emission methanol process of embodiment 10, further comprising the steps of:
    e-6) selective catalytic reduction of the flue gas to remove nitrogen oxides; and
    e-7) pre-heating cold air in a third heat exchanger coil in the convection section.

12. The low-CO2 emission methanol process of embodiment 10 or embodiment 11, further comprising the steps of:
    e-8) cooling the flue gas to below a dew point to form condensate in a condensing portion of the convection section;
    e-9) collecting and removing the condensate from the convection section.

12. The low-CO2 emission methanol process of embodiment 10 or embodiment 11, wherein the entire convection section is maintained at a temperature above a dew point to inhibit condensate formation.

13. The low-CO2 emission methanol process of any preceding embodiment, further comprising the steps of:
    E-1) pre-heating the mixed feed stream in a first heat exchanger coil in a condensing portion of the convection section to cool the flue gas to below a dew point and form condensate;
    E-2) collecting and removing the condensate from the convection section;
    E-3) heating the pre-heated hydrocarbon feedstock from the first heat exchanger coil with the flue gas, in a second heat exchanger coil, in a non-condensing portion of the convection section upstream of the first heat exchanger coil with respect to flue gas flow through the convection section, to superheat the mixed feed stream; and
    E-4) reforming the superheated mixed feed stream in at least the radiant section and optionally in a reforming exchanger in the convection section upstream of the second heat exchanger coil with respect to flue gas flow.

15. The low-CO2 emission methanol process of embodiment 14, further comprising:
    E-5) recycling a portion of the collected condensate to the convection section to contact and scrub the flue gas downstream of the first heat exchanger coil; and or
    E-6) collecting the recycled condensate with the condensate from the first heat exchanger coil; and or
    E-7) cooling the recycled condensate prior to contact with the flue gas; and or
    E-8) adding a scrubbing agent to the recycled condensate prior to contact with the flue gas; and or
    E-9) regenerating at least a portion of the collected condensate to recover a carbon dioxide-rich stream and carbon dioxide-lean condensate for the recycling to the convection section; and or
    E-10) passing the scrubbed flue gas through a demister to remove entrained liquid.

16. The low-CO2 emission methanol process of embodiment 14 or embodiment 15, further comprising:
    E-11) preheating the hydrocarbon in a third heat exchanger coil located downstream of the first heat exchanger in the condensing portion of the convection section; and
    E-12) further preheating the hydrocarbon from the third heat exchanger coil in a fourth heat exchanger coil upstream of the second heat exchanger coil in the non-condensing portion of the convection section; and
    E-13) exchanging heat between the preheated hydrocarbon from the fourth heat exchanger coil and the preheated hydrocarbon from the third heat exchanger coil; and
    E-14) combining the hydrocarbon from the fourth heat exchanger coil with the water to form the mixed feed stream for heating in the first heat exchanger coil; and
    E-15) desulfurizing the preheated hydrocarbon from the fourth heat exchanger coil prior to the mixing with the water in step (a).

17. The low-CO2 emission methanol process of embodiment 16, wherein one of the first and second heat exchangers is located in an essentially vertical convection flue section, and the other one of the first and second heat exchangers is located in an essentially horizontal convection flue section.
18. The low-CO2 emission methanol process of embodiment 16, further comprising:
   E-16) inducing a draft of the flue gas downstream of the second heat exchanger coil and upstream of the condensate collection and first heat exchanger coil, and discharging the flue gas downstream from the first heat exchanger into a stack; and or
   E-17) diverting at least a portion of the flue gas, from a location that is downstream of the draft induction and upstream of the condensate collection and first heat exchanger coil, into the stack, and bypassing the condensate collection and first heat exchanger coil; and or
   E-18) controlling the portion of the diverted flue gas using one or more flow dampers to regulate the flow of the diverted portion; and or
   E-19) passing the flue gas downstream of the draft induction through a first portion of the stack, across the first heat exchanger coil, and then into a second portion of the stack located above the first portion, wherein at least one of the one or more dampers is located in the stack between the first and second portions of the stack.
19. The low-CO2 emission methanol process of any preceding embodiment, further comprising preheating air in an air preheat coil in the convection section, and supplying the preheated air to a combustion burner in the radiant section in step (c).
20. The low-CO2 emission methanol process of any preceding embodiment, wherein step (g) comprises generating steam, preheating boiler feed water, heat exchange with air or cooling water, or a combination thereof.
21. The low-CO2 emission methanol process of any preceding embodiment, wherein the CO2-lean syngas stream in step (h) comprises less than 0.1 vol % CO2 or is preferably essentially free of CO2.
22. The low-CO2 emission methanol process of embodiment 21, wherein step (h) comprises contacting the cooled syngas with a CO2 solvent, preferably an alkanolamine, more preferably methyl diethanolamine.
23. The low-CO2 emission methanol process of embodiment 22, wherein step (h) comprises contacting the cooled syngas with the $CO_2$ solvent in an absorber, and wherein the CO2 is stripped from the solvent in a stripper, wherein the stripper is operated at a lower pressure and/or a higher temperature than the absorber.
24. The low-CO2 emission methanol process of any preceding embodiment, wherein step (i) comprises methanol synthesis with a carbon efficiency of equal to or greater than 95%, preferably equal to or greater than 97%.
25. The low-CO2 emission methanol process of any preceding embodiment, wherein the carbon-lean fuel stream in step (c) consists of or consists essentially of the hydrogen-rich stream from step (l) and the remaining portion of the tail gas stream from step (n).
26. The low-CO2 emission methanol process of embodiment 24, wherein the hydrocarbon feed stock from step (a) and the portion of the tail gas stream from step (m) are supplied to the reforming step (b) at a rate wherein the reforming step (b) produces excess hydrogen for step (l) in an amount, together with the tail gas purge in step (n), that matches the fuel requirements in step (c).
27. The low-CO2 emission methanol process of any preceding embodiment, further comprising condensate stripping from the cooled syngas stream from step (g) upstream from the absorber-stripper unit in step (h), preferably wherein the fusel oil stream from step (j) is supplied to the condensate stripping step.
28. A low-CO2 emissions methanol production apparatus, comprising:
   a mixing station to mix a hydrocarbon feed stock with water and form a mixed feed stream;
   a reformer in a reforming furnace comprising a radiant section and a convection section to reform the mixed feed stream and form a syngas stream:
   an air intake and a carbon-lean fuel stream to fire one or more burners in the radiant section;
   a flue to pass flue gas from the radiant section and through the convection section:
   one or more convection section heat exchangers to cool the flue gas in the convection section;
   an optional particulate removal unit in the convection section to remove particulates from the flue gas:
   a stack to discharge the cooled flue gas from the convection section, wherein the cooled flue gas is lean in CO2 (preferably less than 3 vol %, more preferably less than 1.5 vol %, and even more preferably less than 1 vol %, dry basis);
   one or more process heat exchangers to cool the syngas stream;
   an absorber-stripper unit to directly receive (preferably without any shift converter) the cooled syngas stream and produce a CO2 rich stream and a CO2-lean syngas stream;
   a compressor to recirculate the CO2-lean syngas stream in a methanol reactor loop at a higher pressure than the reformer and produce a methanol-rich stream;
   a methanol wash unit to recover a methanol product, a condensate stream, and a fusel oil stream from the methanol-rich stream;
   a pressure swing adsorption unit to receive a purge stream from the methanol reactor loop to produce a hydrogen-rich stream and a hydrogen-lean tail gas stream:
   a line to supply the hydrogen-rich stream from the pressure swing adsorption unit to the one or more burners;
   a line to supply at least a portion (preferably 90% or more, e.g., 90-95%) of the tail gas stream to the hydrocarbon feed stock;
   a line for purging a remaining portion (preferably 10% or less, e.g., 5-10%) of the tail gas stream to the carbon-lean fuel stream.
29. The low-CO2 emission methanol production apparatus of embodiment 28, wherein the hydrocarbon feed stock comprises natural gas and wherein the mixed feed stream preferably comprises a molar ratio of steam to carbon from 1 to 5, more preferably from 1.8 to 2.5.
30. The low-CO2 emission methanol production apparatus of embodiment 28 or embodiment 29, wherein the reformer comprises:
   one or more pre-reformers in convection heat exchange relationship with the flue gas from the radiant section receiving the mixed feed stream to form a partially reformed feedstock, or one or more pre-reformers disposed externally to the convection section and receiving pre-heated mixed feed from a coil, disposed in the convection section in convection heat exchange relationship with the flue gas from the radiant section, to form a partially reformed feedstock; and a primary reformer disposed in the radiant section to receive the partially reformed feedstock to produce the syngas stream.

31. The low-CO2 emission methanol production apparatus of embodiment 30, wherein the one or more pre-reformers are disposed externally of the convection section, and further comprising a preheat exchange coil disposed in the convection section to pre-heat the partially reformed stream from the one or more pre-reformers for supply to the primary reformer.

32. The low-CO2 emission methanol production apparatus of any of embodiments 28-31, wherein the reformer is operable with an efficiency of at least 90%, preferably at least 92%, and more preferably at least 94%.

33. The low-CO2 emission methanol production apparatus of any of embodiments 28-32, wherein the reformer is operable with a crossover temperature of 566° C. (1050° F.) or less and a reformer outlet temperature of at least 902° C. (1655° F.).

34. The low-CO2 emission methanol production apparatus of any of embodiments 28-33, wherein a ratio of air to fuel produces a flame temperature equal to or greater than 2500° K.

35. The low-CO2 emission methanol production apparatus of any of embodiments 28-34, further comprising:
a first heat exchanger coil in the convection section for pre-heating the hydrocarbon feed stock;
a saturator for saturating the pre-heated hydrocarbon feed stock;
a second heat exchanger coil in the convection section upstream of the first heat exchanger coil with respect to flue gas flow through the convection section, to superheat the mixed feed stream;
one or more pre-reformers disposed in the convection section in heat exchange relationship with the flue gas from the radiant section, upstream of the second heat exchanger coil with respect to flue gas flow for pre-reforming the superheated mixed feed stream and forming a pre-reformed feed stream;
an optional third heat exchanger disposed in the convection section upstream from the one or more pre-reformers with respect to flue gas flow to pre-heat the pre-reformed feed stream; and
a line to supply the pre-reformed feed stream to the reformer.

35. The low-CO2 emission methanol production apparatus of any of embodiments 28-34, further comprising:
a first heat exchanger coil in the convection section for pre-heating the hydrocarbon feed stock;
a saturator for saturating the pre-heated hydrocarbon feed stock;
a second heat exchanger coil in the convection section upstream of the first heat exchanger coil with respect to flue gas flow through the convection section, to superheat the mixed feed stream;
one or more pre-reformers disposed externally of the convection section and receiving the mixed feed stream from a feed preheat coil disposed in the convection section upstream of the second heat exchanger coil with respect to flue gas flow for pre-reforming the superheated mixed feed stream and forming a pre-reformed feed stream;
an optional third heat exchanger disposed in the convection section upstream from the one or more pre-reformers with respect to flue gas flow to pre-heat the pre-reformed feed stream; and
a line to supply the pre-reformed feed stream to the reformer.

37. The low-CO2 emission methanol production apparatus of embodiment 35 or embodiment 36, further comprising:
a selective catalytic reduction unit downstream from the first heat exchanger coil with respect to flue gas flow through the convection section to remove nitrogen oxides from the flue gas; and
a cold air preheater disposed downstream from the selective catalytic reduction unit with respect to flue gas flow through the convection section.

38. The low-CO2 emission methanol process of any of embodiments 35 to 37, further comprising:
a heat exchanger in the convection section for cooling the flue gas to below a dew point to form condensate in a condensing portion of the convection section; and
a line for removing the condensate from the convection section.

39. The low-CO2 emission methanol process of any of embodiments 35 to 37, wherein the entire convection section is free of condensate.

40. The low-CO2 emission methanol production apparatus of any of embodiments 28-39, further comprising:
a first heat exchanger coil in a condensing portion of the convection section to pre-heat the mixed feed stream and cool the flue gas to below a dew point and form condensate;
a reservoir to collect and a line to remove the condensate from the convection section;
a second heat exchanger coil disposed in a non-condensing portion of the convection section upstream of the first heat exchanger coil with respect to flue gas flow through the convection section, to heat the pre-heated hydrocarbon feed stream from the first heat exchanger coil with the flue gas and superheat the mixed feed stream; and
wherein the reformer comprises a pre-reformer in heat exchange relationship with the convection section upstream of the second heat exchanger coil with respect to flue gas flow and a primary reformer in the radiant section.

41. The low-CO2 emission methanol production apparatus of embodiment 40, further comprising:
a line for recycling a portion of the collected condensate to the convection section to contact and scrub the flue gas downstream of the first heat exchanger coil; and or
a reservoir for collecting the recycled condensate with the condensate from the first heat exchanger coil; and or
a heat exchanger for cooling the recycled condensate prior to contact with the flue gas; and or
a scrubbing agent added to the recycled condensate prior to contact with the flue gas; and or
a regenerator to regenerate at least a portion of the collected condensate to recover a carbon dioxide-rich stream and carbon dioxide-lean condensate for the recycling to the convection section; and or
a demister to receive the scrubbed flue gas and remove entrained liquid.

42. The low-CO2 emission methanol production apparatus of embodiment 40 or embodiment 41, further comprising:

a third heat exchanger coil located downstream of the first heat exchanger in the condensing portion of the convection section for preheating the hydrocarbon;

a fourth heat exchanger coil upstream of the second heat exchanger coil in the non-condensing portion of the convection section for preheating the hydrocarbon from the third heat exchanger coil:

an intercooler for exchanging heat between the preheated hydrocarbon from the fourth heat exchanger coil and the preheated hydrocarbon from the third heat exchanger coil;

wherein the mixing station combines the hydrocarbon from the fourth heat exchanger coil with the water to form the mixed feed stream for heating in the first heat exchanger coil; and a desulfurizer for desulfurizing the preheated hydrocarbon from the fourth heat exchanger coil prior to the mixing with the water.

43. The low-CO2 emission methanol production apparatus of embodiment 42, wherein one of the first and second heat exchangers is located in an essentially vertical convection flue section, and the other one of the first and second heat exchangers is located in an essentially horizontal convection flue section.

44. The low-CO2 emission methanol production apparatus of embodiment 42, further comprising:

a fan for inducing a draft of the flue gas downstream of the second heat exchanger coil and upstream of the condensate collection and first heat exchanger coil, and discharging the flue gas downstream from the first heat exchanger into a stack; and or a diverter flue for diverting at least a portion of the flue gas, from a location that is downstream of the draft induction and upstream of the condensate collection and first heat exchanger coil, into the stack, and bypassing the condensate collection and first heat exchanger coil; and or a damper for controlling the portion of the diverted flue gas using one or more flow dampers to regulate the flow of the diverted portion and pass the flue gas downstream of the draft induction through a first portion of the stack, across the first heat exchanger coil, and then into a second portion of the stack located above the first portion, wherein at least one of the one or more dampers is located in the stack between the first and second portions of the stack.

45. The low-CO2 emission methanol production apparatus of any of embodiments 28-44, further comprising an air preheat coil in the convection section and a line for supplying preheated air from the air preheat coil to a combustion burner in the radiant section.

46. The low-CO2 emission methanol production apparatus of any of embodiments 28-45, wherein the one or more process heat exchangers generate steam, preheat boiler feed water, exchange heat with air or cooling water, or a combination thereof.

47. The low-CO2 emission methanol production apparatus of any of embodiments 28-46, wherein the CO2-lean syngas stream comprises less than 0.1 vol % CO2 or is preferably essentially free of CO2.

48. The low-CO2 emission methanol production apparatus of embodiment 47, wherein the absorber-stripper unit comprises a CO2 solvent, preferably an alkanolamine, more preferably methyl diethanolamine.

49. The low-CO2 emission methanol production apparatus of embodiment 48, wherein the stripper is operated at a lower pressure and/or a higher temperature than the stripper.

50. The low-CO2 emission methanol production apparatus of any of embodiments 28-49, wherein the methanol reactor loop operates with a carbon efficiency of equal to or greater than 95%, preferably equal to or greater than 97%.

51. The low-CO2 emission methanol production apparatus of any of embodiments 28-50, wherein the carbon-lean fuel stream consists essentially of or consists of the hydrogen-rich stream from the pressure swing adsorption unit and the remaining portion of the tail gas stream.

52. The low-CO2 emission methanol production apparatus of embodiment 51, wherein the hydrocarbon feed stock and the remaining portion of the tail gas stream match the fuel requirements for reforming at a rate that produces excess hydrogen to meet the firing requirements of the reformer.

53. The low-CO2 emission methanol production apparatus of any of embodiments 28-52, further comprising a condensate stripper for stripping condensate from the cooled syngas stream from the one or more process heat exchangers, and preferably a line to supply the fusel oil stream from the methanol wash unit to the condensate stripper.

54. The invention of any preceding embodiment (especially embodiments 9 and 34) wherein the air is not humidified, preferably wherein the air has a low humidity.

55. The invention of any preceding embodiment wherein a crossover temperature is greater than 621° C. (1150° F.), preferably greater than 621° C. (1150° F.) up to 649° C. (1200° F.).

EXAMPLE

Embodiments of the invention are illustrated by the following hypothetical example. A 1497 tonnes/day (1650 STPD) methanol plant as shown in FIGS. 1 and 2 with the externally disposed pre-reformers 108C, 108D of FIG. 3 is simulated and has the mass balance given in Table 1 below. The syngas composition before and after CO2 removal is shown in Table 2. The plant uses a pre-reformer in the convection section and a fired steam methane reformer in the radiant section with a crossover temperature (xot) of 566° C. (1050° F.) and a reformer outlet temperature (rcot) of 902° C. (1655° F.).

The steam:carbon ratio is 2.2. The reforming duty is 267.97 MW (914.35 mmBtu/hr), and the normal firing is 284.57 MW (970.99 mmBtu/hr) (design 341.58 MW (1165.18 mmBtu/hr)), for an efficiency of 94.17%. The total natural gas feed and fuel (0) is 562.38 MW (1918.93 mmBtu/hr). The energy requirements are 9.008 kWh/kg MeOH (27.91 mmBtu/ST MeOH, LHV) and 10.154 kWh/kg MeOH (31.46 mmBtu/ST MeOH, HHV).

The stack gas emissions are calculated as follows. The normal fuel flow is 337,208 kg/h (743,416 lb/hr, design 404649 kg/h (892,099 lb/hr)) and requires a stoichiometric amount of air at 31.426 kg air/kg fuel. A 10% excess of air is used for an adiabatic flame temperature of 2199° C. (3990° F.) at 34.57 kg air/kg fuel and produces 35.57 kg flue gas/kg fuel. The flue gas composition (wet basis) and normal/design flow rates are shown in Table 3 below. It is seen that the CO2 emissions are 30,451 TPY, compared to a base case using natural gas as fuel of 252,242 TPY, or a reduction of 88%.

Although only a few exemplary embodiments have been described in detail above, those skilled in the art will readily appreciate that many modifications are possible in the example embodiments without materially departing from this disclosure. For example, any embodiments specifically described may be used in any combination or permutation with any other specific embodiments described herein. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' or 'step for' together with an associated function without the recitation of structure.

TABLE 1

Methanol Plant Mass Balance

| Mass Balance | NG Feed | NG Fuel | PSA TG Rec. | Proc. Stm. | Tot. Ref. Inputs | Proc. Con. | $CO_2$ Prod | MeOH Rxr In | MeOH Prod |
|---|---|---|---|---|---|---|---|---|---|
| $10^3$ lbmol/hr | 5.60 | 0.0 | 2.03 | 14.97 | 33.66 | 8.11 | 1.26 | 24.29 | 4.29 |
| $10^3$ lb/hr | 93.75 | 0 | 27.40 | 269.67 | 390.83 | 146.10 | 55.50 | 189.24 | 137.50 |
| S/C | | | | 2.20 | 2.20 | | | | |
| Atom Balance ||||||||||
| C, $10^3$ mol/hr | 5.67 | 0 | 1.14 | 0 | 6.82 | 0.001 | 1.26 | 6.89 | 4.29 |
| H, $10^3$ mol/hr | 22.16 | 0 | 5.72 | 29.94 | 57.81 | 16.22 | 0 | 41.60 | 17.16 |
| O, $10^3$ mol/hr | 0.18 | 0 | 0.23 | 14.97 | 15.38 | 8.11 | 2.52 | 7.27 | 4.29 |
| Composition ||||||||||
| MeOH, mol % | | | | | | | | | 100.0 |
| O2, mol % | | | 3.82 | | | | | | |
| N2, mol % | 0.24 | | | | | | | | |
| CO, mol % | | | 5.69 | | | 0.01 | | | |
| CO2, mol % | 1.62 | | 5.94 | | | 0.01 | | | |
| H2, mol % | | | 0.84 | | | 0.02 | | | |
| CH4, mol % | 96.86 | | 33.99 | | | | | | |
| H2O, mol % | | | 49.71 | 100.0 | | 99.97 | | | |
| Heavier HC, mol % | 1.28 | | | | | | | | |
| Total | 100.0 | | 100.0 | 100.0 | | 100.0 | | | 100.0 |

| Mass Balance | PSA H2 Fuel | PSA TG Fuel | LP Purge | Fusel Oil | Rxn H2O | Purge to PSA | Tot. Outputs |
|---|---|---|---|---|---|---|---|
| $10^3$ lbmol/hr | 8.80 | 0.22 | 0.01 | 0.22 | 0.02 | 2.25 | |
| $10^3$ lb/hr | 17.74 | 3.04 | 0.33 | 4.07 | 0.31 | 30.45 | 374.26 |
| S/C | | | | | | | |
| Atom Balance ||||||||
| C, $10^3$ mol/hr | 0 | 0.14 | 0.001 | 0.01 | 0 | 0.27 | 6.83 |
| H, $10^3$ mol/hr | 17.60 | 0.64 | 0.004 | 0.47 | 0.03 | 4.88 | 57.85 |
| O, $10^3$ mol/hr | 0 | 0.03 | 0.001 | 0.22 | 0.02 | 0.05 | 15.42 |
| Composition ||||||||
| MeOH, mol % | | 3.82 | 20.07 | 0.54 | | 0.78 | |
| O2, mol % | | | | | | | |
| N2, mol % | | 5.69 | 0.35 | | | 1.16 | |
| CO, mol % | | 5.94 | 1.21 | | | 1.21 | |
| CO2, mol % | | 0.84 | 10.61 | | | 0.17 | |
| H2, mol % | 100.0 | 33.99 | 18.77 | | | 86.54 | |
| CH4, mol % | | 49.71 | 31.42 | | | 10.13 | |
| H2O, mol % | | | | 98.09 | 100.0 | 0.01 | |
| Heavier HC, mol % | | | 17.56 | 1.38 | | 0 | |
| Total | 100.0 | 100.0 | 100.0 | 100.0 | 100.0 | 100.0 | |

TABLE 2

Syngas composition and flow rate

| Syngas Composition | | Before $CO_2$ Removal | After $CO_2$ Removal |
|---|---|---|---|
| MeOH | mol % | 0.00% | 0.00% |
| N2 | mol % | 0.50% | 0.53% |
| CO | mol % | 16.80% | 17.67% |
| CO2 | mol % | 5.74% | 0.84% |
| H2 | mol % | 72.31% | 76.06% |
| CH4 | mol % | 4.45% | 4.68% |

TABLE 2-continued

Syngas composition and flow rate

| Syngas Composition | | Before CO2 Removal | After CO2 Removal |
|---|---|---|---|
| H2O | mol % | 0.20% | 0.21% |
| Heavier | mol % | 0.00% | 0.00% |
| Total | | 100.00% | 100.00% |
| Total Moles | MPH | 25550 | 24287 |

TABLE 3

Flue Gas Composition and Flow Rates

| Constituent | Flue Gas Composition (wet basis) | | Flue Gas Flow (lb/hr) | |
|---|---|---|---|---|
| | Mol % | Wt % | Normal | Design |
| O2 | 1.58 | 2.03 | 15064.7 | 18077.6 |
| N2 | 65.24 | 73.46 | 546099.8 | 655319.8 |
| CO2 | 0.44 | 0.78 | 5793.6 | 6952.3 |
| H2O | 32.74 | 23.71 | 176242.9 | 211491.4 |
| SO2 | 0.00 | 0.00 | 0.0 | 0.0 |
| Mol. Wt. | 24.88 | | | |

What is claimed is:

1. A low-CO2 emission methanol process, comprising the steps of:
a) mixing a hydrocarbon feed stock with water to form a mixed feed stream;
b) reforming the mixed feed stream in a reforming furnace comprising a radiant section and a convection section to form a syngas stream;
c) supplying air and a carbon-lean fuel stream comprising hydrogen to fire the radiant section;
d) passing flue gas from the radiant section to the convection section;
e) cooling the flue gas in the convection section and optionally removing particulates from the flue gas;
f) discharging the cooled flue gas, wherein the flue gas is lean in CO2;
g) cooling the syngas stream;
h) passing the cooled syngas stream directly to an absorber-stripper unit to produce a CO2 rich stream and a CO2-lean syngas stream;
i) compressing and passing the CO2-lean syngas stream to a methanol reactor loop to produce a methanol-rich stream, wherein the methanol reactor loop comprises a methanol synthesis reactor, a methanol recovery section to recover a crude methanol stream and a recycle syngas stream, and a recycle compressor to compress the recycle syngas stream to a pressure of the reactor, wherein the pressure of the reactor is higher than a pressure of the mixed feed stream in step (b);
j) processing the crude methanol stream in a methanol wash unit to recover a methanol product, a condensate stream, and a fusel oil stream;
k) supplying a purge stream from the methanol reactor loop to a pressure swing adsorption unit to obtain a hydrogen-rich stream and a hydrogen-lean tail gas stream;
l) supplying the hydrogen-rich stream to the carbon-lean fuel stream in step (c);
m) supplying at least a portion of the tail gas stream from step (k) to the hydrocarbon feed stock in step (a);
n) purging a remaining portion of the tail gas stream from step (l) to the carbon-lean fuel stream in step (c).

2. The low-CO2 emission methanol process of claim 1, further comprising the steps of:
e-1) pre-heating the hydrocarbon feed stock in a first heat exchanger coil in the convection section;
e-2) wherein the mixing in step (a) comprises saturating the pre-heated hydrocarbon feed stock from step (e-1);
e-3) heating the mixed feed stream from step (e-2) with the flue gas in a second heat exchanger coil in the convection section upstream of the first heat exchanger coil with respect to flue gas flow through the convection section, to superheat the mixed feed stream;
e-4) pre-reforming the superheated mixed feed stream in one or more pre-reformers disposed in the convection section in heat exchange relationship with the flue gas, or disposed externally of the convection section receiving the mixed feed stream from a preheating coil disposed in the convection section, upstream of the second heat exchanger coil with respect to flue gas flow, to form a partially reformed stream;
e-5) optionally pre-heating the partially reformed stream, in a third heat exchanger coil in the convection section upstream of the one or more pre-reformers with respect to flue gas flow through the convection section; and
b-2) reforming the partially reformed feed stream in the radiant section.

3. The low-CO2 emission methanol process of claim 2, further comprising the steps of:
e-6) selective catalytic reduction of the flue gas to remove nitrogen oxides; and
e-7) pre-heating cold air in a third heat exchanger coil in the convection section.

4. The low-CO2 emission methanol process of claim 2, further comprising the steps of:
e-8) cooling the flue gas to below a dew point to form condensate in a condensing portion of the convection section;
e-9) collecting and removing the condensate from the convection section.

5. The low-CO2 emission methanol process of claim 2, wherein the entire convection section is maintained at a temperature above a dew point to inhibit condensate formation.

6. The low-CO2 emission methanol process of claim 1, wherein the reforming step (b) comprises:
b-1) pre-reforming the mixed feed stream to form a partially reformed feed stream; and
b-2) primary reforming of the partially reformed feed stream in the radiant section of the reformer.

7. The low-CO2 emission methanol process of claim 6 wherein the pre-reforming is in one or more pre-reformers disposed in the convection section in heat exchange relationship with the flue gas from the radiant section.

8. The low-CO2 emission methanol process of claim 6 wherein the pre-reforming is in one or more pre-reformers disposed externally of the convection section and receiving the mixed feed stream from a coil disposed in the convection section.

9. The low-CO2 emission methanol process of claim 1, further comprising the steps of:
E-1) pre-heating the mixed feed stream in a first heat exchanger coil in a condensing portion of the convection section to cool the flue gas to below a dew point and form condensate;
E-2) collecting and removing the condensate from the convection section;

E-3) heating the pre-heated hydrocarbon feedstock from the first heat exchanger coil with the flue gas, in a second heat exchanger coil, in a non-condensing portion of the convection section upstream of the first heat exchanger coil with respect to flue gas flow through the convection section, to superheat the mixed feed stream; and E-4) reforming the superheated mixed feed stream in at least the radiant section and optionally in a reforming exchanger in the convection section upstream of the second heat exchanger coil with respect to flue gas flow.

10. The low-CO2 emission methanol process of claim 9, further comprising:

E-5) recycling a portion of the collected condensate to the convection section to contact and scrub the flue gas downstream of the first heat exchanger coil; and or E-6) collecting the recycled condensate with the condensate from the first heat exchanger coil; and or E-7) cooling the recycled condensate prior to contact with the flue gas; and or E-8) adding a scrubbing agent to the recycled condensate prior to contact with the flue gas; and or E-9) regenerating at least a portion of the collected condensate to recover a carbon dioxide-rich stream and carbon dioxide-lean condensate for the recycling to the convection section; and or E-10) passing the scrubbed flue gas through a demister to remove entrained liquid.

11. The low-CO2 emission methanol process of claim 1, wherein the CO2-lean syngas stream in step (h) comprises less than 0.1 vol % CO2.

12. The low-CO2 emission methanol process of claim 11, wherein step (h) comprises contacting the cooled syngas with the $CO_2$ solvent in an absorber, and wherein the CO2 is stripped from the solvent in a stripper, wherein the stripper is operated at a lower pressure and/or a higher temperature than the absorber.

13. The low-CO2 emission methanol process of claim 1, wherein the carbon-lean fuel stream in step (c) consists of or consists essentially of the hydrogen-rich stream from step (l) and the remaining portion of the tail gas stream from step (n).

14. The low-CO2 emission methanol process of claim 13, wherein the hydrocarbon feed stock from step (a) and the portion of the tail gas stream from step (m) are supplied to the reforming step (b) at a rate wherein the reforming step (b) produces excess hydrogen for step (l) in an amount, together with the tail gas purge in step (n), that matches the fuel requirements in step (c).

15. The low-CO2 emission methanol process of claim 1, wherein the hydrocarbon feed stock comprises natural gas and wherein the mixed feed stream comprises a molar ratio of steam to carbon from 1 to 5.

16. The low-CO2 emission methanol process of claim 1, wherein the reforming step (b) comprises:

B-1) supplying the mixed feed stream to a first pre-reformer to form a first partially reformed feed stream;

B-2) supplying the first partially reformed feed stream to a second pre-reformer to form a second partially reformed feed stream;

B-3) passing the second partially reformed feed stream to the radiant section of the reforming furnace to produce the syngas stream.

17. The low-CO2 emission methanol process of claim 1, wherein the reforming step has an efficiency of at least 90%.

18. The low-CO2 emission methanol process of claim 1, wherein the reforming step (b) comprises a crossover temperature of 566° C. (1050° F.) or less and a reformer outlet temperature of at least 902° C. (1655° F.).

19. The low-CO2 emission methanol process of claim 1, wherein a ratio of air to fuel in step (c) produces a flame temperature equal to or greater than 2500° K.

20. The low-CO2 emission methanol process of claim 1, wherein step (i) comprises methanol synthesis with a carbon efficiency of equal to or greater than 95%.

21. The low-CO2 emission methanol process of claim 1, further comprising condensate stripping from the cooled syngas stream from step (g) upstream from the absorber-stripper unit in step (h).

22. A low-CO2 emission methanol production apparatus, comprising:

a mixing station to mix a hydrocarbon feed stock with water and form a mixed feed stream;

a reformer in a reforming furnace comprising a radiant section and a convection section to reform the mixed feed stream and form a syngas stream;

an air intake and a carbon-lean fuel stream to fire one or more burners in the radiant section;

a flue to pass flue gas from the radiant section and through the convection section;

one or more convection section heat exchangers to cool the flue gas in the convection section;

an optional particulate removal unit in the convection section to remove particulates from the flue gas;

a stack to discharge the cooled flue gas from the convection section, wherein the cooled flue gas is lean in CO2;

one or more process heat exchangers to cool the syngas stream;

an absorber-stripper unit to directly receive the cooled syngas stream and produce a CO2 rich stream and a CO2-lean syngas stream;

a compressor to recirculate the CO2-lean syngas stream in a methanol reactor loop at a higher pressure than the reformer and produce a methanol-rich stream;

a methanol wash unit to recover a methanol product, a condensate stream, and a fusel oil stream from the methanol-rich stream;

a pressure swing adsorption unit to receive a purge stream from the methanol reactor loop to produce a hydrogen-rich stream and a hydrogen-lean tail gas stream;

a line to supply the hydrogen-rich stream from the pressure swing adsorption unit to the one or more burners;

a line to supply at least a portion of the tail gas stream to the hydrocarbon feed stock; and a line for purging a remaining portion of the tail gas stream to the carbon-lean fuel stream.

23. The low-CO2 emission methanol production apparatus of claim 22, wherein the reformer comprises:

one or more pre-reformers receiving the mixed feed stream to form a partially reformed feedstock; and a primary reformer disposed in the radiant section to receive the partially reformed feedstock to produce the syngas stream.

24. The low-CO2 emission methanol production apparatus of claim 23, wherein the one or more pre-reformers are disposed in the convection section in heat exchange relationship with flue gas from the radiant section.

25. The low-CO2 emission methanol production apparatus of claim 23, wherein the one or more pre-reformers are disposed externally of the convection section, and further comprising a preheat exchange coil disposed in the convection section to pre-heat the partially reformed stream from the one or more pre-reformers for supply to the primary reformer.

26. The low-CO2 emission methanol production apparatus of claim 22, wherein the hydrocarbon feed stock comprises natural gas and wherein the mixed feed stream comprises a molar ratio of steam to carbon from 1 to 5.

\* \* \* \* \*